US010071359B2

(12) United States Patent
Kung et al.

(10) Patent No.: US 10,071,359 B2
(45) Date of Patent: Sep. 11, 2018

(54) HIGH-SPEED ON DEMAND MICROFLUIDIC DROPLET GENERATION AND MANIPULATION

(71) Applicant: The Regents of the University of California, Oakland, CA (US)

(72) Inventors: Yu-Chun Kung, Los Angeles, CA (US); Pei-Yu E. Chiou, Los Angeles, CA (US); Ting-Hsiang S. Wu, Culver City, CA (US); Yue Chen, Los Angeles, CA (US); Michael A. Teitell, Tarzana, CA (US)

(73) Assignee: The Regents of the University of California, Oakland, CA (US)

(*) Notice: Subject to any disclaimer, the term of this patent is extended or adjusted under 35 U.S.C. 154(b) by 112 days.

(21) Appl. No.: 14/775,611

(22) PCT Filed: Mar. 13, 2014

(86) PCT No.: PCT/US2014/026185
§ 371 (c)(1),
(2) Date: Sep. 11, 2015

(87) PCT Pub. No.: WO2014/151658
PCT Pub. Date: Sep. 25, 2014

(65) Prior Publication Data
US 2016/0051958 A1    Feb. 25, 2016

Related U.S. Application Data

(60) Provisional application No. 61/798,516, filed on Mar. 15, 2013.

(51) Int. Cl.
*B01J 19/00* (2006.01)
*B01L 3/00* (2006.01)
(Continued)

(52) U.S. Cl.
CPC ....... *B01J 19/0046* (2013.01); *B01L 3/0265* (2013.01); *B01L 3/502784* (2013.01);
(Continued)

(58) Field of Classification Search
CPC .......... B01J 19/0046; B01J 2219/00587; B01J 2219/00599; B01J 2219/00713;
(Continued)

(56) References Cited

U.S. PATENT DOCUMENTS 6,143,496 A    11/2000   Brown et al.
7,582,482 B2    9/2009   Dasgupta et al.
(Continued)

FOREIGN PATENT DOCUMENTS

CN    1521500 A       8/2004
JP    H05-240872 A    9/1993
(Continued)

OTHER PUBLICATIONS

Jamshaid el a/., (Mar. 8, 2013) "Controllable Active Micro Droplets Merging Device Using Horizontal Pneumatic Micro Valves", Micromachines, 4(1): 34-48. (Year: 2013).*
(Continued)

*Primary Examiner* — Jennifer Wecker
(74) *Attorney, Agent, or Firm* — Tom Hunter; Weaver Austin Villeneuve & Sampson LLP

(57) ABSTRACT

Methods and devices for the formation and/or merging of droplets in microfluidic systems are provided. In certain embodiments a microfluidic droplet merger component is provided that comprises a central channel comprising a plurality of elements disposed and spaced to create a plurality of lateral passages that drain a carrier fluid out of a fluid stream comprising droplets of a first fluid contained in the carrier fluid; and a deformable lateral membrane valve disposed to control the width of said center channel.

12 Claims, 14 Drawing Sheets

(51) Int. Cl.
*G01N 35/08* (2006.01)
*B01L 3/02* (2006.01)
*B01L 7/00* (2006.01)

(52) U.S. Cl.
CPC ..... *G01N 35/08* (2013.01); *B01J 2219/00587* (2013.01); *B01J 2219/00599* (2013.01); *B01J 2219/00713* (2013.01); *B01J 2219/00722* (2013.01); *B01J 2219/00756* (2013.01); *B01L 7/52* (2013.01); *B01L 2200/0673* (2013.01); *B01L 2300/0816* (2013.01); *B01L 2300/0867* (2013.01); *B01L 2300/123* (2013.01); *B01L 2400/0655* (2013.01); *B01L 2400/086* (2013.01)

(58) Field of Classification Search
CPC ... B01J 2219/00722; B01J 2219/00756; B01L 2200/0673; B01L 2300/0816; B01L 2300/0867; B01L 2300/123; B01L 2400/0655; B01L 2400/086; B01L 3/0265; B01L 3/502784; B01L 7/52
See application file for complete search history.

(56) References Cited

U.S. PATENT DOCUMENTS

| | | | |
|---|---|---|---|
| 8,062,903 | B2 | 11/2011 | Chiu et al. |
| 8,127,624 | B2 | 3/2012 | Hashimoto et al. |
| 8,136,553 | B2 | 3/2012 | Baroud et al. |
| 8,206,994 | B2 | 6/2012 | Baroud et al. |
| 8,268,633 | B2 | 9/2012 | Ramsey et al. |
| 8,383,061 | B2 | 2/2013 | Prakash et al. |
| 8,506,905 | B2 | 8/2013 | Takeuchi et al. |
| 8,506,907 | B2 | 8/2013 | Angelescu |
| 8,563,325 | B1 | 10/2013 | Bartsch et al. |
| 8,592,215 | B2 | 11/2013 | Quake et al. |
| 9,176,504 | B2 | 11/2015 | Chiou et al. |
| 9,364,831 | B2 | 6/2016 | Chiou et al. |
| 2002/0005354 | A1 | 1/2002 | Spence et al. |
| 2002/0029814 | A1 | 3/2002 | Unger et al. |
| 2002/0037499 | A1 | 3/2002 | Quake et al. |
| 2002/0166582 | A1 | 11/2002 | O'Connor et al. |
| 2003/0198523 | A1 | 10/2003 | Bohm et al. |
| 2006/0073035 | A1 | 4/2006 | Sundararajan |
| 2006/0128006 | A1 | 6/2006 | Gerhardt et al. |
| 2006/0177348 | A1 | 8/2006 | Yasuda et al. |
| 2006/0246575 | A1 | 11/2006 | Lancaster et al. |
| 2008/0032295 | A1 | 2/2008 | Toumazou et al. |
| 2008/0196778 | A1 | 8/2008 | Baroud et al. |
| 2009/0090422 | A1 | 4/2009 | Baroud et al. |
| 2010/0173394 | A1* | 7/2010 | Colston, Jr. ............ B01F 3/0807 435/287.2 |
| 2011/0030808 | A1 | 2/2011 | Chiou et al. |
| 2011/0059556 | A1 | 3/2011 | Strey et al. |
| 2011/0114190 | A1 | 5/2011 | Wen et al. |
| 2011/0177586 | A1 | 7/2011 | Ismagilov et al. |
| 2012/0236299 | A1 | 9/2012 | Chiou et al. |
| 2013/0183210 | A1 | 7/2013 | Wiyatno et al. |
| 2014/0212986 | A1 | 7/2014 | Angelescu et al. |
| 2015/0174576 | A1* | 6/2015 | Van Vilet ............ B01L 3/0241 506/12 |
| 2016/0158752 | A1 | 6/2016 | Chiou et al. |
| 2016/0296933 | A1 | 10/2016 | Chiou et al. |

FOREIGN PATENT DOCUMENTS

| | | | |
|---|---|---|---|
| JP | 2001-158099 | A | 6/2001 |
| JP | 2003-514236 | A | 4/2003 |
| JP | 2004-65110 | A | 3/2004 |
| JP | 2006-523142 | A | 10/2006 |
| JP | 2007-515936 | A | 6/2007 |
| JP | 2009-100698 | A | 5/2009 |
| JP | 2010-054492 | A | 3/2010 |
| JP | 2010-169551 | A | 8/2010 |
| KR | 10-2009-0119029 | A | 11/2009 |
| WO | WO 01/35071 | A2 | 5/2001 |
| WO | WO 2005/023391 | A2 | 3/2005 |
| WO | WO 2010/092845 | A1 | 8/2010 |
| WO | WO 2012/009320 | A2 | 1/2012 |
| WO | WO 2013/120016 | A2 | 8/2013 |
| WO | WO 2014/151658 | A1 | 9/2014 |

OTHER PUBLICATIONS

U.S. Office Action dated Oct. 10, 2012 issued in U.S. Appl. No. 12/852,320.
U.S. Final Office Action dated Aug. 1, 2013 issued in U.S. Appl. No. 12/852,320.
U.S. Office Action dated Mar. 12, 2014 issued in U.S. Appl. No. 12/852,320.
U.S. Final Office Action dated Jan. 2, 2015 issued in U.S. Appl. No. 12/852,320.
U.S. Office Action dated Jul. 16, 2015 issued in U.S. Appl. No. 12/852,320.
U.S. Notice of Allowance dated Feb. 10, 2016 issued in U.S. Appl. No. 12/852,320.
U.S. Office Action dated Feb. 16, 2017 issued in U.S. Appl. No. 15/094,919.
U.S. Office Action dated Jan. 2, 2014 issued in U.S. Appl. No. 13/370,196.
U.S. Final Office Action dated Aug. 20, 2014 issued in U.S. Appl. No. 13/370,196.
U.S. Advisory Action dated Mar. 5, 2015 issued in U.S. Appl. No. 13/370,196.
U.S. Notice of Allowance dated Jun. 5, 2015 issued in U.S. Appl. No. 13/370,196.
U.S. Notice of Allowance dated Jun. 24, 2015 issued in U.S. Appl. No. 13/370,196.
U.S. Requirement for Restriction/Election dated Sep. 21, 2016 issued in U.S. Appl. No. 14/930,054.
U.S. Office Action dated Dec. 20, 2016 issued in U.S. Appl. No. 14/930,054.
PCT International Search Report and Written Opinion dated Dec. 20, 2013 issued in PCT/US2013/025434.
PCT International Preliminary Report on Patentability and Written Opinion dated Aug. 12, 2014 issued in PCT/US2013/025434.
Australian Patent Examination Report No. 1 dated Sep. 15, 2015 issued in AU 2013216804.
Australian Patent Examination Report No. 2 dated Jun. 6, 2016 issued in AU 2013216804.
Chinese Office Action (brief description in English) dated Jul. 24, 2015 issued in CN 201380016299.3.
Chinese Second Office Action (brief description in English) dated Mar. 16, 2016 issued in CN 201380016299.3.
European Extended Search Report dated Jan. 7, 2016 issued in EP 13 74 6888.
Reply Letter to European Extended Search Report dated Aug. 3, 2016 in EP 13 74 6888.
Japanese Office Action dated Oct. 7, 2016 issued in JP 2014-556753.
Japanese Decision of Rejection dated May 8, 2017 issued in JP 2014-556753.
PCT International Search Report and Written Opinion dated Jul. 9, 2014 issued in PCT/US2014/026185.
PCT International Preliminary Report on Patentability and Written Opinion dated Sep. 15, 2015 issued in PCT/US2014/026185.
Australian Patent Examination Report No. 1 dated Jul. 13, 2017 issued in AU 2014233699.
Chinese Office Action [No Translation] dated May 2, 2017 issued in CN 201480025551.1.
European Extended Search Report dated Oct. 10, 2016 issued in EP 14768515.0.
Applegate, Jr. et al., (2006) "Microfluidic sorting system based on optical waveguide integration and diode laser bar trapping," *Lab on a Chip*, 6:422-426 [Downloaded by University of California—Los Angeles on Apr. 18, 2013 19:29:53. Published on Jan. 20, 2006 on http://pubs.rsc.org | doi:10.1039/B512576F].

(56) References Cited

OTHER PUBLICATIONS

Baret et al., (2009) "Fluorescence-activated droplet sorting (FADS): efficient microfluidic cell sorting based on enzymatic activity," *Lab on a Chip*, 9:1850-1858 [Downloaded by University of California—Los Angeles on Apr. 18, 2013 19:18:09. Published on Apr. 23, 2009 on http://pubs.rsc.org | doi:10.1039/B902504A].

Bransky et al., (2009) "A Microfluidic Droplet Generator based on a Piezoelectric Actuator", *Lab Chip*, 9: 516-520.

Chiou et al., (Jul. 21, 2005) "Massively parallel manipulation of single cells and microparticles using optical images," *Nature*, 436:370-372 [doi:10.1038/nature03831].

Cho et al., (2010) "Human mammalian cell sorting using a highly integrated micro-fabricated fluorescence-activated cell sorter (μFACS)," *Lab on a Chip*, 10:1567-1573 [Downloaded by University of California—Los Angeles on Apr. 18, 2013 19:31:47. Published on Apr. 9, 2010 on http://pubs.rsc.org | doi:10.1039/C000136H].

Di Carlo et al., (Nov. 27, 2007) "Continuous inertial focusing, ordering, and separation of particles in microchannels," *PNAS of the United States of America*, 104(48): 18892-18897.

El-Sayed et al., (2006) "Selective laser photo-thermal therapy of epithelial carcinoma using anti-EGFR antibody conjugated gold nanoparticles," *Cancer Letters*, 239:129-135.

Fu et al., (Jun. 1, 2002) "An integrated microfabricated cell sorter," *Analytical Chemistry*, 74(11):2451-2457.

Fu et al., (Nov. 1999) "A microfabricated fluorescence-activated cell sorter," *Nature Biotechnology*, 17:1109-1111 [© 1999 Nature America Inc. http://biotech.nature.com].

Godin et al., (2008) "Microfluidics and photonics for Bio-System-on-a-Chip: A review of advancements in technology towards a microfluidic flow cytometry chip," *J. Biophoton.*, 1(5):355-376. [DOI 10.1002/jbio.200810018].

Guo et al., (2012) "Droplet Microfluidics for High-Throughput Biological Assays", *Lab Chip*, 12: 2146-2155.

He et al., (2005) "Selective Encapsulation of Single Cells and Subcellular Organelles into Picoliter- and Femtoliter-Volume Droplets," *Analytical Chemistry*, 77(6):1539-1544.

Hellman et al., (Jun. 15, 2007) "Laser-Induced Mixing in Microfluidic Channels," *Analytical Chemistry*, 79(12):4484-4492.

Hessel et al., (2004) *Chemical Micro Process Engineering:Modelling and Reactions*, New York: Wiley-VCH Verlag GmbH & Co. KGaA, Weinheim, 36 pages.

Ho et al., (2005) "Micromachined electrochemical T-switches for cell sorting applications," *Lab on a Chip*, 5:1248-1258 [Downloaded by University of California—Los Angeles on Apr. 18, 2013 19:05:23. Published on Sep. 21, 2005 on http://pubs.rsc.org | doi:10.1039/B507575K].

Holmes et al., (2007) "Bead-based immunoassays using a microchip flow cytometer," *Lab on a Chip*, 7:1048-1056 [Downloaded by University of California—Los Angeles on Apr. 18, 2013 19:09:02. Published on Jun. 14, 2007 on http://pubs.rsc.org | doi:10.1039/B707507N].

Hsiung et al., (2006) "Micro-droplet formation utilizing microfluidic flow focusing and controllable moving-wall chopping techniques," *J. Micromechanics and Microengineering*, 16:2403-2410 [Downloaded on Apr. 18, 2013 at 19:11, http://iopscience.iop.org/0960-1317/16/11/022].

Huang et al., (2006) "Cancer Cell Imaging and Photothermal Therapy in the Near-Infrared Region by Using Gold Nanorods," *J. Am. Chemical Society*, 128:2115-2120.

Huh et al., (2003) "Reversible Switching of High-Speed Air-Liquid Two-Phase Flows Using Electrowetting-Assisted Flow-Pattern Change," *JACS*, 125:14678-14679.

Hur et al., (2010) "Sheathless inertial cell ordering for extreme throughput flow cytometry," *Lab on a Chip*, 10:274-280 [Downloaded by University of California—Los Angeles on Apr. 18, 2013 19:12:27. Published on Dec. 18, 2009 on http://pubs.rsc.org | doi:10.1039/B919495A].

Ibrahim et al., (2003) "High-speed cell sorting: fundamentals and recent advances," *Current Opinion in Biotechnology*, 14(1):5-12.

Idota et al., (2005) "Microfluidic Valves Comprising Nanolayered Thermoresponsive Polymer-Grafted Capillaries," *Advanced Materials*, 17:2723-2727.

Irimia, Daniel and Toner, Mehmet (Mar. 2006) "Cell handling using microstructured membranes," *Lab on a Chip*, 6:345-352 [Downloaded by University of California—Los Angeles on Apr. 18, 2013 19:10:43. Published on Feb. 8, 2006 on http://pubs.rsc.org | doi:10.1039/B515983K].

Jamshaid et al., (Mar. 8, 2013) "Controllable Active Micro Droplets Merging Device Using Horizontal Pneumatic Micro Valves", *Micromachines*, 4(1): 34-48.

Jensen, K. (Jun. 25, 1998) "Chemical kinetics—Smaller, faster chemistry," *Nature*, 393:735-737.

Jensen, K.F. (Jan. 2001) "Microreaction engineering—is small better?" *Chemical Engineering Science*, 56:293-303.

Kim et al., (Jul. 2007) "Novel platform for minimizing cell loss on separation process: Droplet-based magnetically activated cell separator," *Review of Scientific Instruments*, 78:074301-1-7.

Leary, James F., (2005) "Ultra high-speed sorting," *International Society for Analytical Cytology, Cytometry Part A* 67A:76-85.

Li et al., (2010) "Two Same-Sized Droplets Coalescence by Laser-Induced Cavitation Bubbles," *14th International Conference on Miniaturized Systems for Chemistry and Life Sciences*, Oct. 3-7, 2010, Groningen, The Netherlands, pp. 1088-1090.

Li et al., (2011) "Fast on-demand droplet fusion using transient cavitation bubbles," *Lap on a Chip*, 11:1879-1885 [Published on Apr. 12, 2011. Downloaded by Korea Advanced Institute of Science & Technology / KAIST on Jan. 11, 2013 00:55:20.].

Link et al., (2006) "Electric Control of Droplets in Microfluidic Devices", *Angew. Chem. Int. Ed.*, 45(16): 2556-2560.

Marcus et al., (May 1, 2006) "Microfluidic single-cell mRNA isolation and analysis," *Analytical Chemistry*, 78(9):3084-3089.

Mehta et al., (Jan. 5-8, 2009) "Magnetic Nanowire-Enhanced Optomagnetic Tweezers," *Proceeding of the 2009 4th IEEE International Conference on Nano/Micro Engineered and Molecular Systems*, Shenzhen, China, pp. 1004-1007.

Melin et al., (2007) "Microfluidic Large-Scale Integration: The Evolution of Design Rules for Biological Automation," *Annual Review of Biophysics and Biomolecular Structure*, 36:213-231 [Annu. Rev. Biophys. Biomol. Struct. 2007.36:213-231. Downloaded from www.annualreviews.org by University of California—Los Angeles—Law Library UCLA on Apr. 18, 2013. For personal use only].

Niu et al., (2008) "Pillar-induced droplet merging in microfluidic circuits" *Lab Chip*, 8(11): 1837-1841.

Panaro et al., (Feb. 2005) "Micropillar array chip for integrated white blood cell isolation and PCR," *Biomolecular Engineering*, 21:157-162.

Park et al., (2011) "High-speed droplet generation on demand driven by pulse laser-induced cavitation," *Lab on a Chip*, 11(6):1010-1012, 3 pages.

Park et al., (2011) "High-speed droplet generation on demand driven by pulse laser-induced cavitation," *Lab on a Chip*, 11(6):1010-1012, 9 pages [NIH Public Access, NIH-PA Author Manuscript].

Park et al., (Jan. 2010) "A pulse laser-driven microfluidic device for ultra-fast droplet generation on demand and single-cells encapsulation," *14th International Conference on Miniaturized Systems for Chemistry and Life Sciences*, Groningen, The Netherlands, pp. 2129-2131.

Pitsillides et al., (Jun. 2003) "Selective cell targeting with light-absorbing microparticles and nanoparticles," *Biophys J*, 84(6):4023-4032.

Shirasaki et al., (Feb. 1, 2006) "On-Chip Cell Sorting System Using Laser-Induced Heating of a Thermoreversible Gelation Polymer to Control flow," *Analytical Chemistry*, 78(3):695-701.

Sun et al., (2007) "Design, simulation and experiment of electroosmotic microfluidic chip for cell sorting," *Sens. Actuators A*. 133(2):340-348.

Tandiono et al., (2010) "Creation of cavitation activity in a microfluidic device through acoustically driven capillary waves," *Lab Chip*, 10:1848-1855.

(56) References Cited

OTHER PUBLICATIONS

Vogel et al., (Dec. 2005) "Mechanisms of femtosecond laser nanosurgery of cells and tissues," *Applied Physics B—Lasers and Optics*, 81:1015-1047.

Wang et al., (2007) "High-density microfluidic arrays for cell cytotoxicity analysis," *Lab on a Chip*, 7:740-745 [Downloaded by University of California—Los Angeles on Apr. 18, 2013 19:50:05. Published on Apr. 4, 2007 on http://pubs.rsc.org | doi:10.1039/B618734J].

Wang et al., (Jan. 2005) "Microfluidic sorting of mammalian cells by optical force switching," *Nature Biotechnology*, 23(1):83-87.

Wu et al., (Jan. 18, 2010) "Image patterned molecular delivery into live cells using gold particle coated substrates," *Optics Express*, 18(2):938-946.

Wu et al., (2012) "Pulsed laser triggered high speed microfluidic fluorescence activated cell sorter," *Lab on a Chip*, 12:1378-1383 [Downloaded by University of California—Los Angeles on Apr. 18, 2013 19:33:06. Published on Feb. 15, 2012 on http://pubs.rsc.org I doi:10.1039/C2LC21084C].

Wu et al., (Oct. 6, 2008) "Pulsed laser triggered high speed microfluidic switch," *Appl. Phys. Lett.* 93, 144102-1-3. [Downloaded Oct. 10, 2008 to 131.252.222.209. Redistribution subject to AIP license or copyright; see http://apl.aip.org/apl/copyright.jsp].

Xavier Casadevall i Solvas and Andrew deMello, (2011) "Droplet Microfluidics: Recent Developments and Future Applications", *Chemical Communications*, 47: 1936-1942.

Xu, Jie and Attinger, Daniel, (2008) "Drop on demand in a microfluidic chip," *J. Micromechanics and Microengineering*, 18:065020, 11 pp. [downloaded on Apr. 18, 2013 at 19:43, http://iopscience.iop.org/0960-1317/18/6/065020].

Yao et al., (Nov./Dec. 2005) "Elevation of plasma membrane permeability by laser irradiation of selectively bound nanoparticles," *J Biomed Opt*, 10(6):064012-1-064012-8.

Yoshida et al., (Mar. 2005) "Enhancement of Chemical Selectivity by Microreactors," *Chemical Engineering & Technology*, 28(3):259-266.

Zeng et al., (2009) "Microvalve-actuated precise control of individual droplets in microfluidic devices," *Lab on a Chip*, 9:1340-1343 [Downloaded by University of California—Los Angeles on Apr. 18, 2013 19:50:54. Published on Mar. 27, 2009 on http://pubs.rsc.org | doi:10.1039/B821803J].

Zhong et al., (2008) "A microfluidic processor for gene expression profiling of single human embryonic stem cells," *Lab on a Chip*, 8:68-74 [Downloaded on Apr. 18, 2013 19:20:57. Published on Nov. 2, 2007 on http://pubs.rsc.org | doi:10.1039/B712116D].

Zhong et al., (2008) "Microfluidic Devices for Investigating Stem Cell Gene Regulation via Single-Cell Analysis," *Current Medicinal Chemistry*, 15(28):2897-2900.

Zwaan et al., (2007) "Controlled cavitation in microfluidics," *Phys. Rev. Lett.*, 98:2545, 4 pages.

U.S. Final Office Action dated Nov. 3, 2017 issued in U.S. Appl. No. 15/094,919.

U.S. Final Office Action dated Nov. 1, 2017 issued in U.S. Appl. No. 14/930,054.

Chinese Office Action [No Translation] dated Nov. 29, 2017 issued in CN 201480025551.1.

Australian Patent Examination Report No. 2 dated May 3, 2018 issued in AU 2014233699.

Japanese Office Action dated Apr. 2, 2018 issued in JP 2016-502075.

* cited by examiner

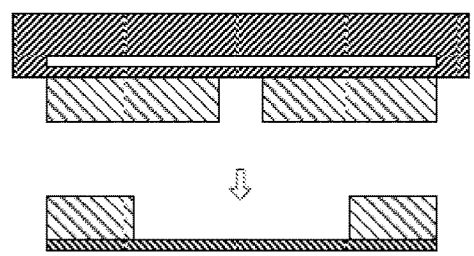
Figure 5T
Fig. 9T
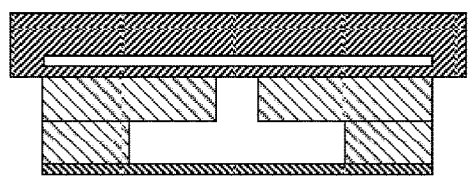
Fig. 9U
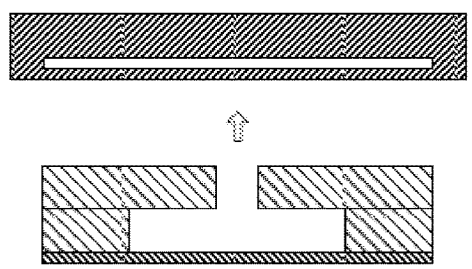
Fig. 9V

HIGH-SPEED ON DEMAND MICROFLUIDIC DROPLET GENERATION AND MANIPULATION

CROSS-REFERENCE TO RELATED APPLICATIONS

This application is a U.S. 371 National Phase of PCT/US2014/026185, filed Mar. 13, 2014, which claims benefit of and priority to U.S. Ser. No. 61/798,516, filed on Mar. 15, 2013, all of which are incorporated herein by reference in their entirety for all purposes.

STATEMENT OF GOVERNMENTAL SUPPORT

This invention was made with government support under Grant No. 0901154, awarded by the National Science Foundation. The government has certain rights in the invention.

BACKGROUND

Over the last decade microfluidic systems have developed into valuable instrumental platforms for performing high throughput chemistry and biology (deMello (2006) *Nature*, 442: 394-402). The ability to controllably merge droplets within segmented flow systems is of high importance when performing complex chemical or biological analyses (Shestopalov et al. (2004) *Lab Chip*, 4: 316-321). Unfortunately, the controlled merging of multiple droplets in a sequential fashion is not straightforward. Although the emulsions produced in microfluidic systems are thermodynamically metastable, the process of merging has not proven to be predictable, due to subtle variations in interfacial tension, surface topography of microchannels, and fluidic properties such as of droplet size, viscosity, and velocity (see, e.g., Fuerstman et al. (2007) *Science*, 315: 828-832).

Droplet merging is important or essential in many applications including sequential reactions (Kim et al. (2006) *Anal. Chem.*, 78(23): 8011-8019), multiple step manipulation of cells (He et al. (2005) *Anal. Chem.*, 77(6): 1539-1544), high-throughput bioassays (Srisa-Art et al. (2007) *Anal. Chem.*, 79: 6682-6689), and the like. Additionally, the ability to merge and split droplets or bubbles in a high throughput manner cab impact the use of bubble logic systems for exchanging chemical and electronic information (Prakash and Gershenfeld (2007) *Science*, 315(5813): 832-835).

In typical droplet merging processes, relatively large time and spatial scales are involved. For example, timescales may range from the sub-microsecond regime for some chemical reactions to many hours and even days for cell-based assays. Similarly, large spatial scales also exist, for example, between the droplets to be merged and between the droplets and the component interfaces that interact to drive the merging process.

Several techniques have been developed to merge droplets. These are either active and involve components such as electric fields (Priest et al. (2006) *Appl. Phys. Lett.*, 89: 134101:1-134101:3; Ahn et al. (2006) *Appl. Phys. Lett.*, 88: 264105), or passive and utilize the surface properties (Fidalgo et al. (2007) *Lab Chip*, 7(8): 984-986) or structure (Tan et al. (2004) *Lab Chip*, 4(4): 292-298) of the fluidic conduit.

SUMMARY

In various embodiments in various embodiments, a microfluidic droplet merger component (e.g., for integration into microfluidic systems such as lab-on-a-chip systems, and the like) is provided. An illustrative, but noon-limiting droplet merger structure comprises a central channel comprising a plurality of elements (e.g. a micropillar array) disposed and spaced to create a plurality of lateral passages that drain a carrier fluid out of a fluid stream comprising droplets of a first fluid contained in said carrier fluid; and a deformable lateral membrane valve disposed to control the width of said center channel. Trapping and merging of different numbers of droplets can be controlled by the spacing and arrangement of lateral passages and/or elements forming such passages (e.g., the micropillar array structure), the timing, and the constriction size of the deformable lateral membrane valve. The deformable membrane (membrane valve) forms a controllable, variable-sized constriction, e.g., at the downstream of the trapping structure. By controlling the constriction size and timing, different numbers of droplets can be trapped and merged before exiting the device. Also provided are microfluid droplet generators and devices comprising one or more microfluid droplet generators and/or one or more droplet merger structures.

In various aspects, the invention(s) contemplated herein may include, but need not be limited to, any one or more of the following embodiments:

In various aspects, the invention(s) contemplated herein may include, but need not be limited to, any one or more of the following embodiments:

Embodiment 1: A microfluidic droplet merger component, said component including: a central channel including a plurality of elements disposed and spaced to create a plurality of lateral passages that drain a carrier fluid out of a fluid stream including droplets of a first fluid contained in said carrier fluid; and a deformable lateral membrane valve disposed to control the width of said center channel.

Embodiment 2: The droplet merger component of embodiment 1, wherein said membrane valve is a pneumatically actuated lateral membrane valve.

Embodiment 3: The droplet merger component according to any one of embodiments 1-2, wherein the width of said central channel reduces as a function of distance downstream through said plurality of lateral passages.

Embodiment 4: The droplet merger component according to any one of embodiments 1-3, wherein the where the width of said lateral passages is smaller than the width of said central channel at the same location and smaller than the average diameter of a droplet in the central channel.

Embodiment 5: The droplet merger component according to any one of embodiments 1-4, wherein said plurality of elements comprise a micropillar array.

Embodiment 6: The droplet merger component according to any one of embodiments 1-5, wherein said valve is located at or downstream of the last of said plurality of elements.

Embodiment 7: The droplet merger component of embodiment 5, wherein said micropillar array includes pairs of pillars that form lateral channels slanted in a downstream direction.

Embodiment 8: The droplet merger component of embodiment 7, wherein said valve is located at or downstream of the last (downstream) pairs of pillars.

Embodiment 9: The droplet merger component according to any one of embodiments 1-8, wherein said pillars are configured to provide an inter-pillar spacing that ranges from about 0.1 μm to about 100 μm.

Embodiment 10: The droplet merger component according to any one of embodiments 1-8, wherein said pillars are configured to provide an inter-pillar spacing that ranges from about 0.1 µm to about 10 µm.

Embodiment 11: The droplet merger component according to any one of embodiments 1-10, wherein said deformable lateral membrane valve is configured to form a controllable, variable-sized construction at the downstream end of said plurality of elements.

Embodiment 12: The droplet merger component according to any one of embodiments 1-11, wherein said deformable lateral membrane valve is configured to deform horizontally.

Embodiment 13: The droplet merger component according to any one of embodiments 1-11, wherein said deformable lateral membrane valve is configured to deform vertically.

Embodiment 14: The droplet merger component according to any one of embodiments 1-13, wherein said micropillar array is formed from a material selected from the group consisting of glass, metal, ceramic, mineral, plastic, and polymer.

Embodiment 15: The droplet merger component according to any one of embodiments 1-13, wherein said micropillar array is formed from an elastomeric material.

Embodiment 16: The droplet merger component of embodiment 15, wherein said elastomeric material is selected from the group consisting of polydimethylsiloxane (PDMS), polyolefin plastomers (POPs), perfluoropolyethylene (a-PFPE), polyurethane, polyimides, and cross-linked NOVOLAC® (phenol formaldehyde polymer) resin.

Embodiment 17: A microfluidic droplet generator, said generator including: a first microfluidic channel containing a first fluid adjacent to a second microfluidic channel containing a second fluid wherein said first fluid is substantially immiscible in second fluid; and a cavitation channel or chamber where the contents of said cavitation channel or chamber is separated from the contents of said first microfluidic channel by a deformable channel wall or chamber wall, where said cavitation channel or chamber is configured to permit said deformable channel wall or chamber wall to deform when a bubble is formed in said cavitation channel or chamber, and where said cavitation channel or chamber is disposed above or below said first microfluidic channel.

Embodiment 18: The droplet generator of embodiment 17, wherein, said first microfluidic channel is in fluid communication with said second microfluidic channel via a port or a channel.

Embodiment 19: The droplet generator according to any one of embodiments 17-18, where a first portion of said first microfluidic channel is disposed a first distance away from said second microfluidic channel, and a second portion of said first microfluidic channel is disposed a second distance away from said second microfluidic channel and said second distance is less than said first distance.

Embodiment 20: The droplet generator of embodiment 19, wherein said first microfluidic channel includes a third portion disposed so that said second portion is located between said first portion and said third portion and said third portion of said microfluidic channel is located at a third distance away from said second microfluidic channel and said third distance is greater than said second distance.

Embodiment 21: The droplet generator according to any one of embodiments 17-20, where the maximum width of said first microfluidic channel and/or said second microfluidic channel ranges from about 0.1 µm to about 500 µm.

Embodiment 22: The droplet generator according to any one of embodiments 17-20, where the maximum width of said first microfluidic channel and/or said second microfluidic channel ranges from about 50 µm to about 100 µm.

Embodiment 23: The droplet generator according to any one of embodiments 17-20, where the width of said first microfluidic channel and/or said second microfluidic channel is about 100 µm.

Embodiment 24: The droplet generator according to any one of embodiments 17-23, where the maximum depth of said first microfluidic channel and/or said second microfluidic channel ranges from about 0.1 µm to about 500 µm.

Embodiment 25: The droplet generator according to any one of embodiments 17-23, where the maximum depth of said first microfluidic channel and/or said second microfluidic channel ranges from about 40 µm to about 80 µm.

Embodiment 26: The droplet generator according to any one of embodiments 17-23, where the typical depth of said first microfluidic channel and/or said second microfluidic channel is about 50 µm.

Embodiment 27: The droplet generator according to any one of embodiments 17-26, wherein the typical depth of said cavitation channel or chamber ranges from about 100 µm to about 150 µm.

Embodiment 28: The droplet generator according to any one of embodiments 17-27, wherein said droplet generator is configured to generate droplets having a volume ranging from about 1 atto L to about 1 µL.

Embodiment 29: The droplet generator of embodiment 28, wherein said droplet generator is configured to generate droplets having a volume ranging from about 1 pL to about 150 pL.

Embodiment 30: The droplet generator according to any one of embodiments 17-28, wherein said cavitation channel or chamber is a cavitation channel.

Embodiment 31: The droplet generator of embodiment 30, wherein said cavitation channel provides permits the contents of said channel to flow and thereby aid dissipation of a bubble formed therein.

Embodiment 32: The droplet generator according to any one of embodiments 17-31, wherein said cavitation channel or chamber is disposed above said first microfluidic channel.

Embodiment 33: The droplet generator according to any one of embodiments 17-31, wherein said cavitation channel or chamber is disposed below said first microfluidic channel.

Embodiment 34: The droplet generator according to any one of embodiments 17-33, wherein said cavitation channel or chamber contains a dye.

Embodiment 35: The droplet generator according to any one of embodiments 17-33, wherein said cavitation channel or chamber contains light-absorbing nanoparticle and/or microparticles.

Embodiment 36: The droplet generator according to any one of embodiments 17-35, wherein said first microfluidic channel is configured to provide said first fluid under a substantially static pressure to create a stable interface between said first fluid and said second fluid.

Embodiment 37: The droplet generator according to any one of embodiments 17-36, wherein said first fluid includes an aqueous fluid.

Embodiment 38: The droplet generator according to any one of embodiments 17-37, wherein said second fluid includes an oil or an organic solvent.

Embodiment 39: The droplet generator of embodiment 38, wherein said second fluid includes a solvent selected from the group consisting of carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, and 2,2, 4-trimethylpentane.

Embodiment 40: The droplet generator of embodiment 38, wherein said second fluid includes an oil.

Embodiment 41: The droplet generator according to any one of embodiments 17-40, wherein said port or channel includes a nozzle.

Embodiment 42: The droplet generator according to any one of embodiments 17-41, wherein said first and/or second microfluidic channel is formed from a material selected from the group consisting of glass, metal, ceramic, mineral, plastic, and polymer.

Embodiment 43: The droplet generator according to any one of embodiments 17-42, wherein said first and/or second microfluidic channel is formed from an elastomeric material.

Embodiment 44: The droplet generator of embodiment 43, wherein said elastomeric material is selected from the group consisting of polydimethylsiloxane (PDMS), polyolefin plastomers (POPs), perfluoropolyethylene (a-PFPE), polyurethane, polyimides, and cross-linked NOVOLAC® (phenol formaldehyde polymer) resin.

Embodiment 45: The droplet generator according to any one of embodiments 17-44, wherein said generator can provide on-demand droplet generation at a speed of greater than about 1,000, more preferably greater than about 2,000 droplets/sec, more preferably greater than about 4,000 droplets/sec, more preferably greater than about 6,000 droplets/sec, or more preferably greater than about 8,000 droplets/sec.

Embodiment 46: The droplet generator according to any one of embodiments 17-44, wherein said device can provide on-demand droplet generation at a speed ranging from zero droplets/sec, 1 droplets/sec, 2 droplets/sec, about 5 droplets/sec, about 10 droplets/sec, about 20 droplets/sec, about 50 droplets/sec, about 100 droplets/sec, about 500 droplets/sec, or about 1000 droplets/sec, up to about 1,500 droplets/sec, about 2,000 droplets/sec, about 4,000 droplets/sec, about 6,000 droplets/sec, about 8,000 droplets/sec, about 10,000 droplets/sec, about 20,000 droplets/sec, about 50,000 droplets/sec, or about 100,000 droplets/sec.

Embodiment 47: The droplet generator according to any one of embodiments 17-44, wherein said device can provide on-demand droplet generation at a speed of greater than about 1,000, more preferably greater than about 10,000, more preferably greater than about 20,000 droplets/sec, more preferably greater than about 40,000, more preferably greater than about 50,000 droplets/sec, more preferably greater than about 80,000, or more preferably greater than about 100,000 droplets/sec.

Embodiment 48: The droplet generator according to any one of embodiments 17-47, wherein said generator is present in a system including an energy source configured to form a bubble in said cavitation channel or chamber.

Embodiment 49: The droplet generator of embodiment 48, wherein said energy source includes an optical energy source or microwave emitter.

Embodiment 50: The droplet generator of embodiment 48, wherein said energy source includes a laser.

Embodiment 51: The droplet generator of embodiment 50, wherein said energy source includes a pulse laser.

Embodiment 52: The droplet generator according to any one of embodiments 17-51, wherein said generator is disposed on a substrate including a material selected from the group consisting of a polymer, a plastic, a glass, quartz, a dielectric material, a semiconductor, silicon, germanium, ceramic, and a metal or metal alloy.

Embodiment 53: The droplet generator according to any one of embodiments 17-52, wherein said generator is integrated with other microfluidic components.

Embodiment 54: The droplet generator of embodiment 53, wherein said other microfluidic components selected from the group consisting of PDMS channels, wells, valves.

Embodiment 55: The droplet generator of embodiment 53, wherein said generator is a component of a lab-on-a-chip.

Embodiment 56: The droplet generator according to any one of embodiments 17-55, wherein said first fluid includes one or more reagents for polymerase chain reaction (PCR).

Embodiment 57: The droplet generator of embodiment 56, wherein said first fluid includes one or more reagents selected from the group consisting of a PCR primer, a PCR template, a polymerase, and a PCR reaction buffer.

Embodiment 58: A device for the manipulation of microfluidic droplets, said device including a substrate carrying or including: one or more droplet merger components according to any one of embodiments 1-16; and optionally one or more droplet generators according to any one of embodiments 17-57.

Embodiment 59: The device of embodiment 58, wherein said device further includes a controller that controls the amount and timing of constriction of said membrane valve.

Embodiment 60: The device according to any one of embodiments 58-59, wherein said device includes one or more droplet generators according to any one of embodiments 17-57.

Embodiment 61: The device according to any one of embodiments 58-60, wherein said device includes at least two droplet generators.

Embodiment 62: The device of embodiment 61, wherein said device includes at least four droplet generators.

Embodiment 63: The device according to any one of embodiments 61-62, wherein a plurality of droplet generators are configured to share a common second microfluidic channel and to inject droplets into said common second microfluidic channel.

Embodiment 64: The device of embodiment 63, wherein a droplet merger component is disposed to receive and merge droplets from said common second microfluidic channel.

Embodiment 65: A system for the generation of droplets and/or the encapsulation of particles or cells said, said system including a droplet generator according to any one of embodiments 17-57 and an excitation source for forming gas bubbles in a fluid.

Embodiment 66: The system of embodiment 65, wherein said excitation source includes an optical energy source.

Embodiment 67: The system of embodiment 66, wherein said excitation source includes a non-coherent optical energy source.

Embodiment 68: The system of embodiment 66, wherein said excitation source includes a laser.

Embodiment 69: The system according to any one of embodiments 66-68, wherein said system includes an objective lens configured to focus optical energy into said cavitation channel or chamber.

Embodiment 70: The system of embodiment 69, wherein said system includes a half-wave plate.

Embodiment 71: The system according to any one of embodiments 69-70, wherein said system includes a polarizer.

Embodiment 72: The system of embodiment 71, wherein said polarizer includes a polarizing beam splitter cube.

Embodiment 73: The system according to any one of embodiments 66-72, wherein said system includes a controller that adjusts at least one of the timing of occurrence of light pulses emitted by the optical energy source, the frequency of occurrence of pulses emitted by the optical energy source, the wavelength of pulses emitted by the optical energy source, the energy of pulses emitted by the optical energy source, and the aiming or location of pulses emitted by the optical energy source.

Embodiment 74: The system according to any one of embodiments 65-73, wherein said system further includes components for detecting particles, droplets, or cells in said system.

Embodiment 75: The system of embodiment 74, wherein said components comprise an optical detection system, an electrical detection system, a magnetic detection system or an acoustic wave detection system.

Embodiment 76: The system of embodiment 74, wherein said components comprise an optical detection system for detecting a scattering, a fluorescence, or a ramen spectroscopy signal.

Embodiment 77: A method of combining droplets in a microfluidic system, said method including providing a plurality of droplets flowing through a microfluidic channel into the central channel(s) of one or more droplet merger components according to any one of embodiments 1-16 causing the merger of a plurality of droplets.

Embodiment 78: The method of embodiment 77, further including varying the constriction created by said lateral membrane valve to control the timing of droplet merger and/or the number of merged droplets.

Embodiment 79: The method of embodiment 78, wherein said varying the constriction includes operating a controller that pneumatically actuates said lateral membrane valve(s).

Embodiment 80: A method for generating droplets said method including: applying an energy source to a droplet generator according to any one of embodiments 17-57, where said energy source forms bubbles in said cavitation channel or chamber to deform said deformable channel wall or chamber wall and to inject a droplet of said first fluid into said second fluid in said second microfluidic channel.

Embodiment 81: The method of embodiment 80, wherein said utilizing an energy source includes utilizing a laser to excite cavitation bubbles in said cavitation channel or chamber.

Embodiment 82: The method of embodiment 81, wherein said method includes using a controller that adjusts at least one of the timing of occurrence of pulses emitted by a pulsed laser, the frequency of occurrence of pulses emitted by the pulsed laser, the wavelength of pulses emitted by the pulse laser, the energy of pulses emitted by the pulse laser, and the aiming or location of pulses emitted by the pulse laser.

Embodiment 83: The method according to any one of embodiments 80-82, further including generating a plurality of separate and additional cavitation bubbles at a frequency of at least 1000 Hz.

Embodiment 84: The method of embodiment 83, wherein said method is repeated at a frequency of 1 kHz or greater.

Embodiment 85: The method according to any one of embodiments 80-84, wherein said first fluid includes one or more reagents for polymerase chain reaction (PCR).

Embodiment 86: The droplet generator of embodiment 85, wherein said first fluid includes one or more reagents selected from the group consisting of a PCR primer, a PCR template, a polymerase, and a PCR reaction buffer.

Embodiment 87: A method of generating and combining droplets, said method including: providing a device including one or more droplet generators droplet generator according to any one of embodiments 17-57 and one or more droplet merger component(s) according to any one of embodiments 1-16, wherein at least one of said one or more droplet merger component(s) is disposed to receive droplets generated by at least one of said one or more droplet generators; applying an energy source a cavitation channel or chamber of one or more of said one or more droplet generator(s), where said energy source forms bubbles in said cavitation channel or chamber to deform said deformable channel wall or chamber wall and to inject a droplet of said first fluid into said second fluid in said second microfluidic channel; receiving a plurality of droplets generated by said one or more droplet generator(s) in at least one of said one or more droplet merger components where said droplets merger to form a combined droplet fluid.

Embodiment 88: The method of embodiment 87, wherein said device includes a plurality of droplet generators.

Embodiment 89: The method of embodiment 87, wherein said device includes at least three droplet generators.

Embodiment 90: The method according to any one of embodiments 87-89, wherein said device includes a plurality of droplet merger components.

Embodiment 91: The method of embodiment 90, wherein said device includes at least three droplet merger components.

Embodiment 92: The method according to any one of embodiments 87-91, wherein said utilizing an energy source includes utilizing a laser to excite cavitation bubbles in said cavitation channel or chamber.

Embodiment 93: The method of embodiment 92, wherein said method includes using a controller that adjusts at least one of the timing of occurrence of pulses emitted by a pulsed laser, the frequency of occurrence of pulses emitted by the pulsed laser, the wavelength of pulses emitted by the pulse laser, the energy of pulses emitted by the pulse laser, and the aiming or location of pulses emitted by the pulse laser.

Embodiment 94: The method according to any one of embodiments 87-93, further including generating a plurality of separate and additional cavitation bubbles at a frequency of at least 1000 Hz.

Embodiment 95: The method of embodiment 94, wherein said method is repeated at a frequency of 1.2 kHz or greater.

Embodiment 96: The method according to any one of embodiments 87-95, wherein said first fluid includes one or more reagents for polymerase chain reaction (PCR).

Embodiment 97: The method of embodiment 96, wherein said first fluid includes one or more reagents selected from the group consisting of a PCR primer, a PCR template, a polymerase, and a PCR reaction buffer.

Embodiment 98: The method according to any one of embodiments 87-97, wherein said device comprise or is integrated with other microfluidic components.

Embodiment 99: The method of embodiment 98, wherein said other microfluidic components selected from the group consisting of PDMS channels, wells, valves.

Embodiment 100: The method of embodiment 98, wherein said device includes or is integrated with a lab-on-a-chip.

DETAILED DESCRIPTION

Two-phase flow (or multi-phase) systems that can manipulate picoliter (μL) volume droplets in closed channels have broad lab on chip applications. Small droplets allow reduction of reagent consumption, high sensitivity detection, and large scale analysis. Thousands of droplets can be easily generated in a simple two-phase flow channel, and tens or hundreds of channels can be structured in parallel to increase throughput. Droplets can also be programmed to merge, split, and mix at high speed for rapid screening. Commercial systems could achieve 10 million droplet reactions or screening per hour. Applications include a variety of PCR techniques, such as digital PCR, RT-PCR, PCR, single cell analysis, combinatorial chemical synthesis, and the like.

I. On-Demand Lateral Membrane Valve for Passive Droplet Trapping and Merging

Figure 1:
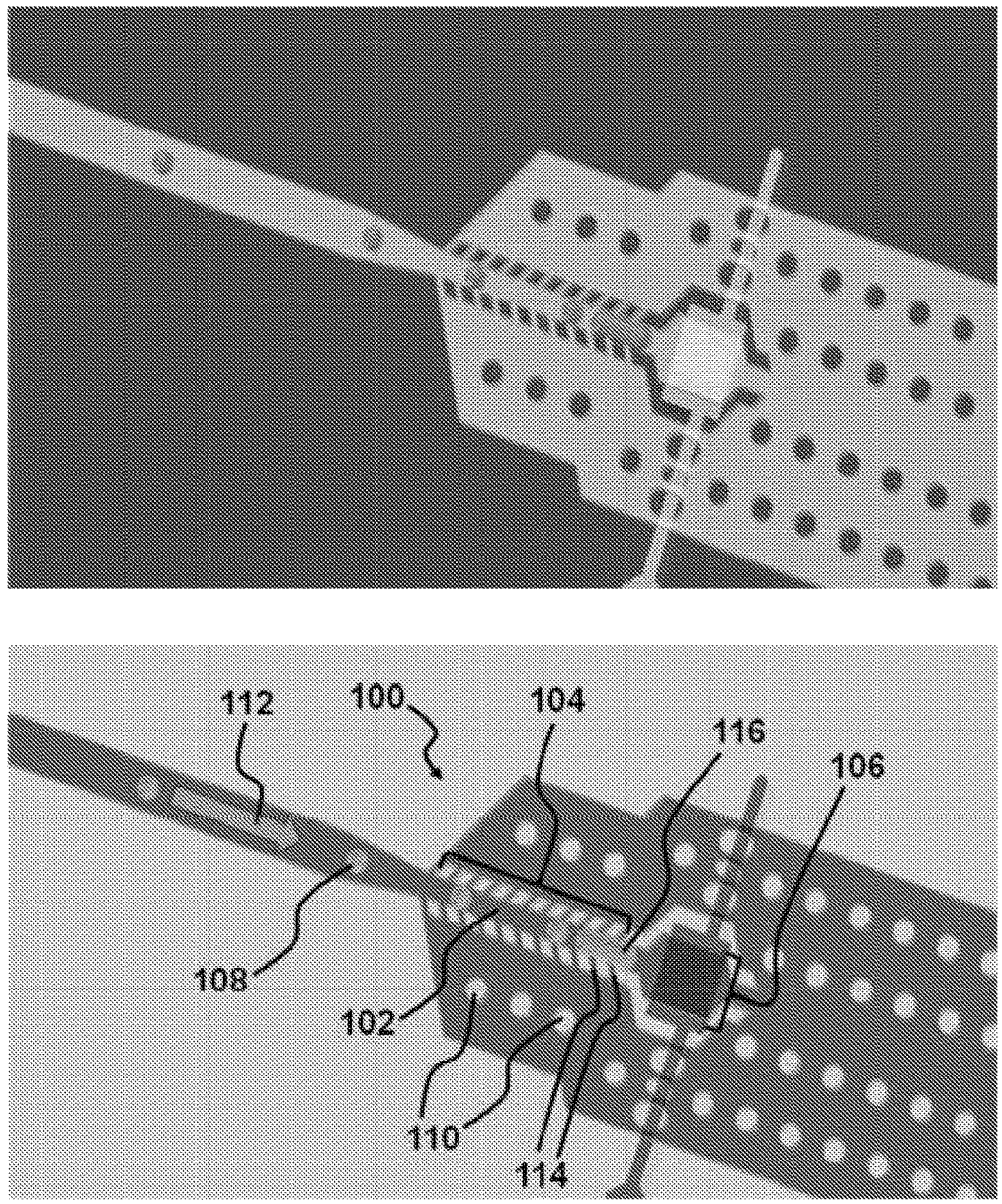
FIG. 1 shows a schematic illustration of a droplet merger module 100 with deformable lateral membrane valves 106. Fluid containing droplets 108 flows in flow direction 112 through a central channel 102. A plurality of elements 104 form lateral channels 114 that drain fluid from between trapped droplets 108 which then merge into a merged droplet 116 and leave behind the drained fluid, e.g. as droplets 110. A pair of pneumatically actuated lateral membrane valves 106 located at the end of the plurality of elements (e.g., pillar structure) is used to change the width of the center channel to control the number of trapped droplets. When a threshold number of droplets is reached, the hydraulic pressure on the merged droplet becomes bigger than the surface tension to release it. No movement of membrane is required, which is the key to enable high speed merging.

In various embodiments a tunable droplet trapping and merging module is provided. One embodiment of such a component/module 100 is illustrated in FIG. 1. As illustrated therein the droplet merger component comprises a central channel 102 comprising a plurality of elements 104 (e.g., an array of pillar structures) disposed and spaced to create a plurality of lateral passages 114 that drain a carrier fluid out of a fluid stream comprising droplets 108 of a first fluid contained in the carrier fluid; and a deformable lateral membrane valve 106 disposed to control the width of the center channel.

Droplets in, for example, a microchannel 118 move in a downstream direction 112. Droplets flowing downstream are trapped in the droplet merging module. The plurality of elements 104 provides lateral passages 114 are used to drain out fluid oil between droplets to merge them. A pair of pneumatically actuated lateral membrane valves 106 located at the downstream end of the plurality of elements can be used to change the width of the flow channel. In various embodiments the width of the central channel reduces as a function of distance downstream through a plurality of lateral passages. In certain embodiments the width ranges from 10 μm to about 1 mm at the upstream end of the component to a width that ranges about 1 μm to about 900 μm where the downstream width is smaller than the upstream width. In certain embodiments the width of the lateral passages is smaller than the width of the central channel at the same location and smaller than the average diameter of a droplet in the central channel.

In certain embodiments the plurality of elements comprise a micropillar array. In certain embodiments the micropillar array comprises pairs of pillars that define the central channel. In certain embodiments the valve is located at or downstream of the last of the plurality of elements (e.g. downstream of the last (downstream) pair of pillars). In certain embodiments the pillars are configured to provide an inter-pillar spacing that ranges from about 0.1 μm to about 100 μm. In certain embodiments the pillars are configured to provide an inter-pillar spacing that ranges from about 0.1 μm to about 10 μm. In certain embodiments the deformable lateral membrane valve is configured to form a controllable, variable-sized construction at the downstream end of said plurality of elements. In certain embodiments the deformable lateral membrane valve is configured to deform vertically.

In various embodiments the deformation of the lateral membrane can be tuned by changing the pneumatic pressure though the vias underneath the deformation chamber. It is noted that in certain embodiments, deformation of the lateral membrane can be regulated by mechanical actuators. For example, in certain embodiments, piezo-linear actuators, electrostatic actuators, and the like can be used to control deformation of the lateral membrane.

Figure 5:
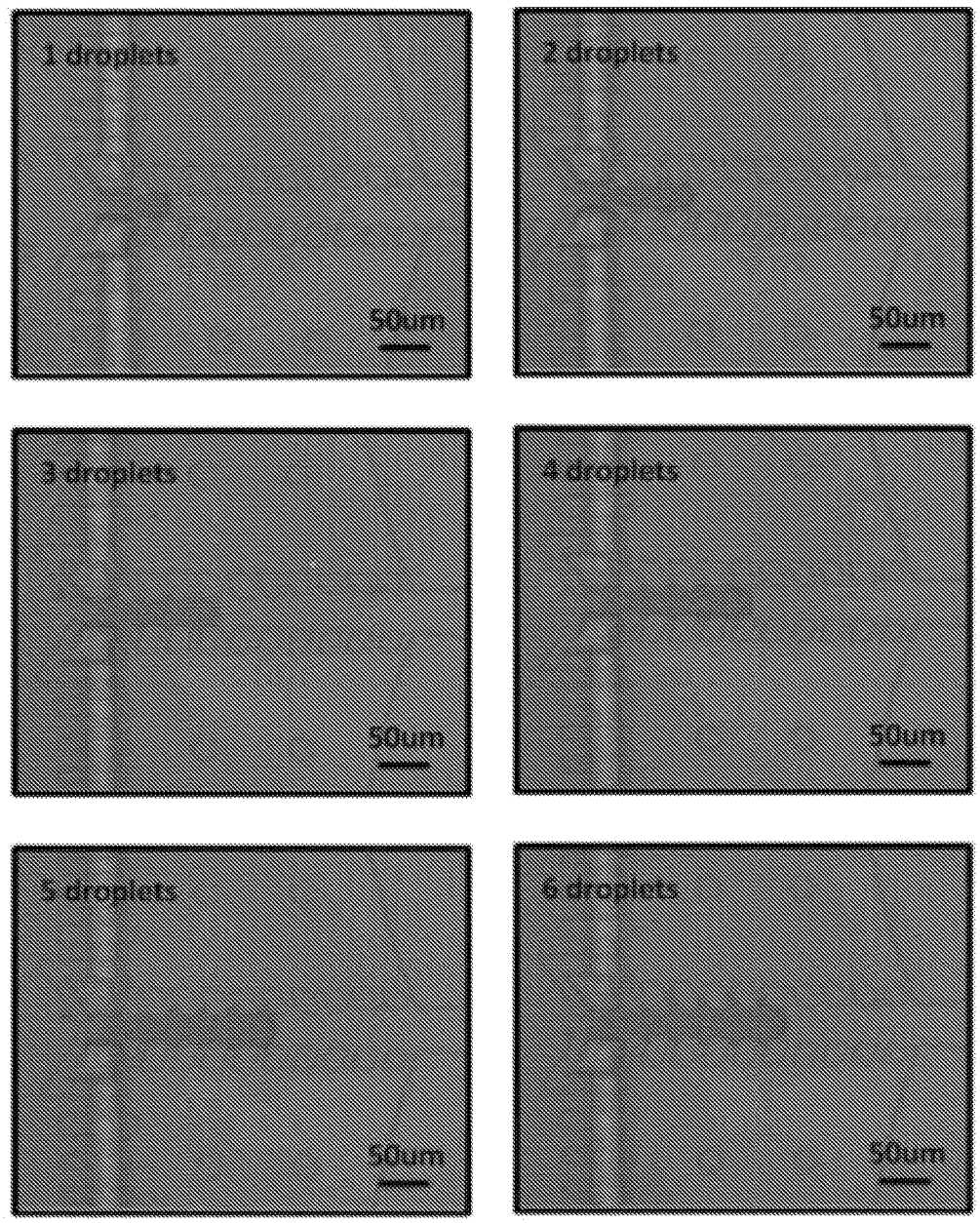
FIG. 5 shows time-resolved images of an illustrative droplet merging process. Up to six droplets have been experimentally trapped and merged on this passive but tunable merging module. In this illustrated embodiment, the merged droplet releases automatically when the number of droplets is larger than 6.
Figure 8:
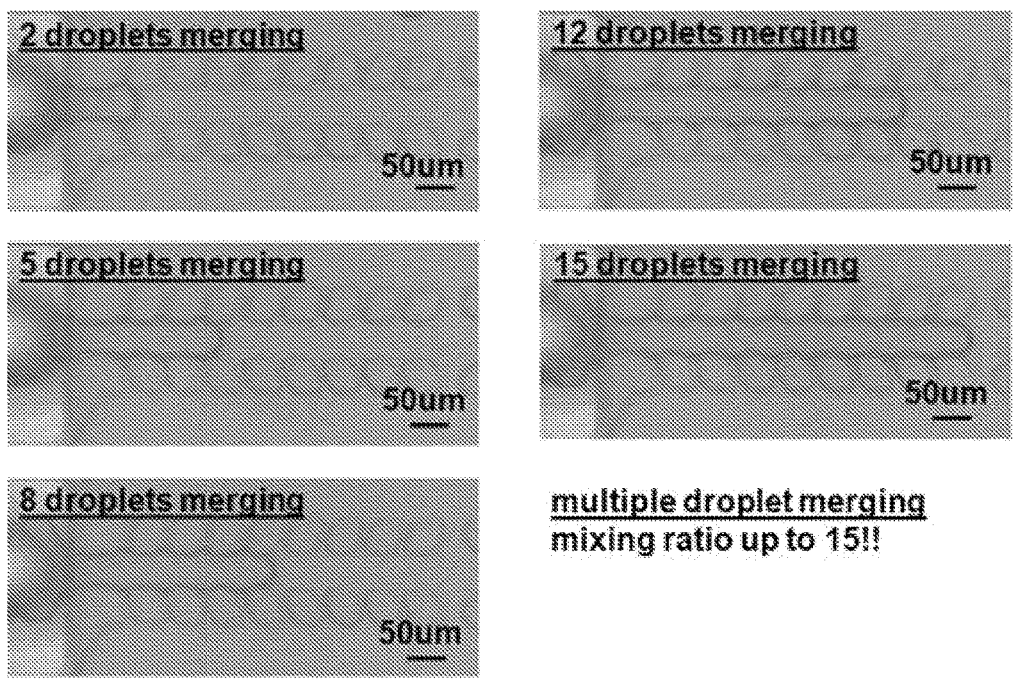
FIG. 8 illustrates multiple droplet trapping and merging with a vertically deformed membrane valve.

The number of droplets trapped in the merging module can be tuned by degree of deformation of the lateral membrane valve. When the number of trapped droplets reaches to its trapping threshold, the fused droplet releases automatically without the need to mechanically deform the membrane valve. Such passive type droplet merger can have high speed since there is no need to deform the mechanical membrane. As illustrated in FIG. 5, six droplets can be passively trapped, merged and released. In some cases where more droplets are required to merge (for example, creating a large combinatorial library), the membrane valve, which in this illustration is deformed vertically can be fully closed to hold more droplets. Up to 15 droplets have been trapped and merged using this mode, as shown in FIG. 8. It will be noted, however, that the methods and devices are not limited to trapping six or 15 droplets. Accordingly in certain embodiments, at least 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30 or more droplets are trapped and merged.

In certain embodiments, where the membrane closing process is slow, the throughput may be lower than about 10 merged droplets/sec.

Figure 3:
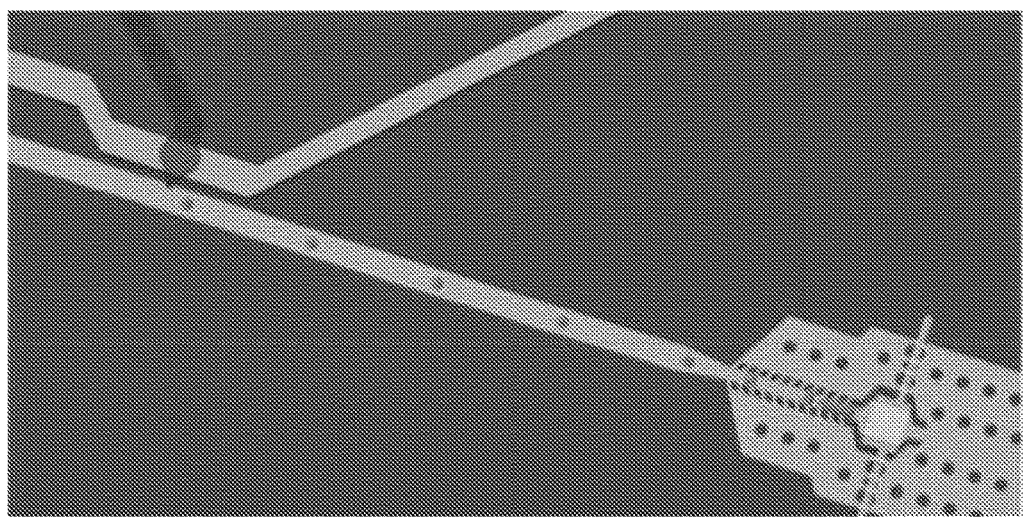
FIG. 3 shows a schematic illustration of an on-demand droplet generation and fusion platform, that integrates a pulse laser induced on-demand membrane valve droplet generator and a lateral membrane valve controlled droplet merging module.

One illustrative, but non-limiting schematic of an integrated droplet generation and merging modules for high speed production of multiplexed droplets is shown in FIG. 3.

In certain embodiments the devices described herein utilize a thin-layer soft lithography process to produce certain structures (e.g., valve membranes). The fabrication of thin layers of, e.g., PDMS is enabled by a novel Pt-PDMS thin film process described in copending provisional application No. 61/616,385, filed on Mar. 27, 2012, and in copending provisional application entitled "CONTINUOUS WHOLE-CHIP 3-DIMENSIONAL DEP CELL SORTER AND RELATED FABRICATION METHOD", filed on Mar. 15, 2013, both of which are incorporated herein for the PtPDMS thin film fabrication processes described therein.

Figure 9A:
FIGS. 9A through 9ZB depict, via simplified cross-sectional views, various stages of a manufacturing technique for producing multi-layer PDMS structures.
Figure 9A:
Figure 9B:
Figure 9B:
Figure 9C:
Figure 9C:
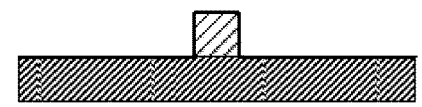
Figure 9D:
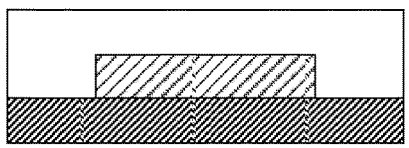
Figure 9D:
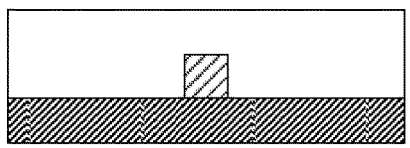
Figure 9E:
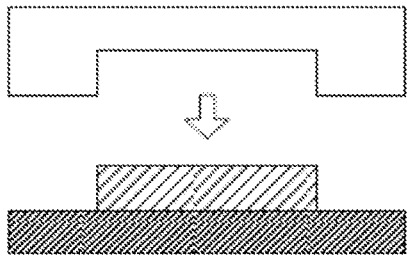
Figure 9E:
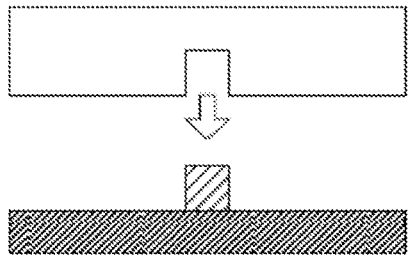
Figure 9F:
Figure 9F:
Figure 9G:
Figure 9G:
Figure 9H:
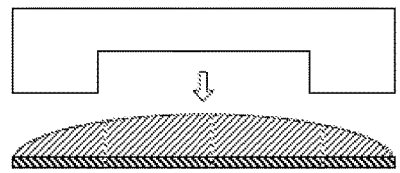
Figure 9H:
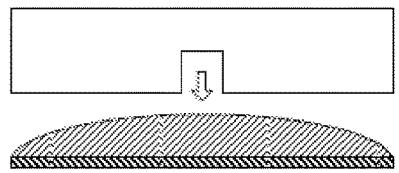
Figure 9I:
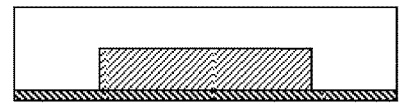
Figure 9I:
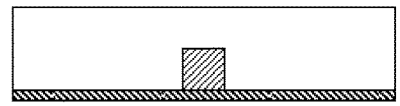
Figure 9J:
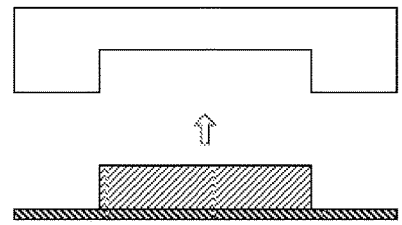
Figure 9J:
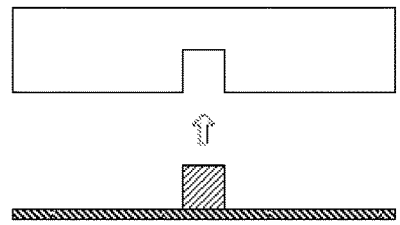
Figure 9K:
Figure 9K:
Figure 9L:
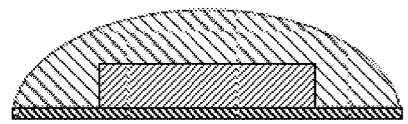
Figure 9L:
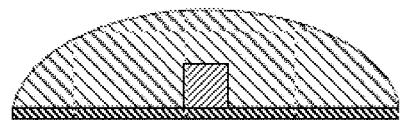
Figure 9M:
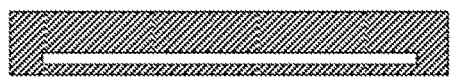
Figure 9M:
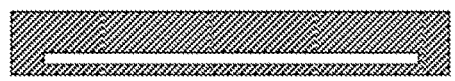
Figure 9M:
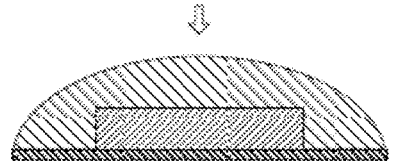
Figure 9M:
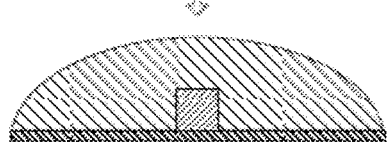
Figure 9N:
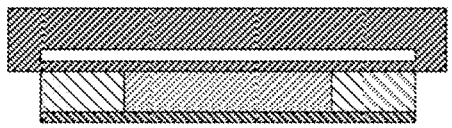
Figure 9N:
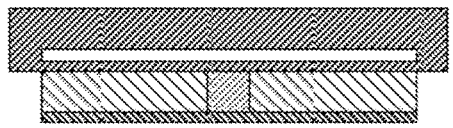
Figure 9O:
Figure 9O:
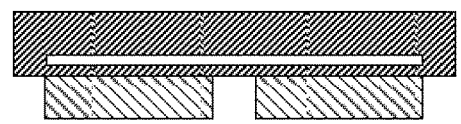
Figure 9O:
Figure 9O:
Figure 9O:
Figure 9O:
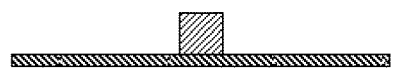
Figure 9P:
Figure 9Q:
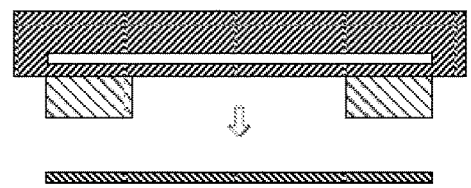
Figure 9R:
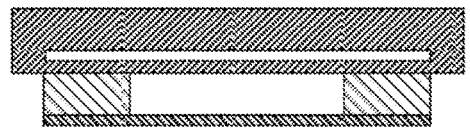
Figure 9S:
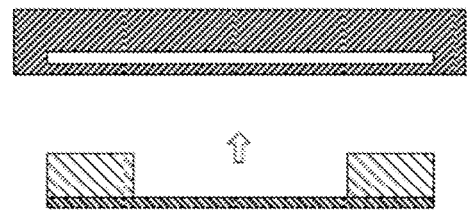
Figure 9W:
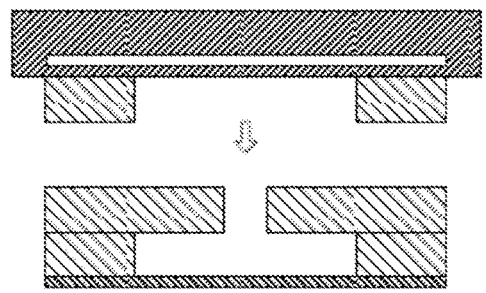
Figure 9X:
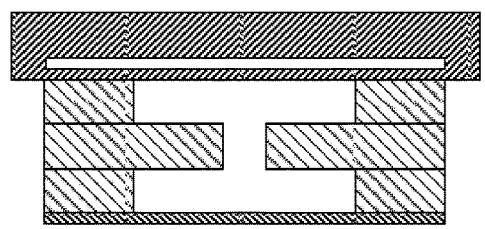
Figure 9Y:
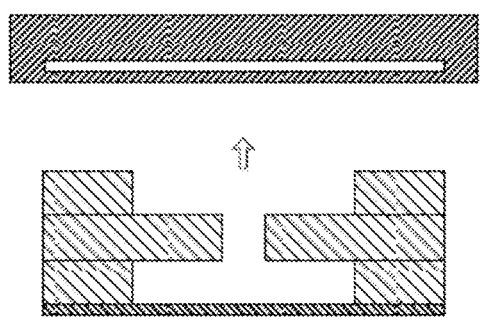
Figure 9Z:
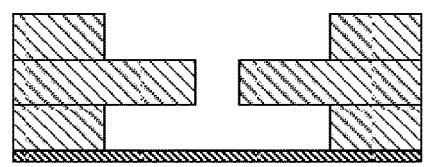
Figure 9Z:
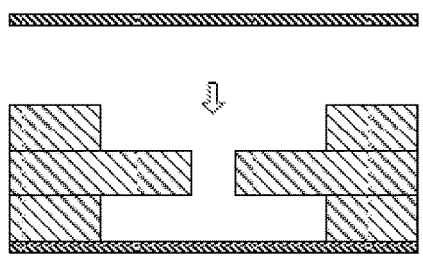
Figure 9Z:
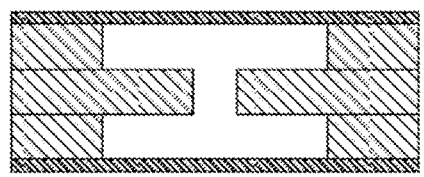

In particular one implementation of this ptPDMS fabrication process is depicted via simplified cross-sectional views in FIGS. 9A through 9ZB. The structure that is being constructed in FIGS. 9A through 9ZB is a portion of a three-dimensional DEP cell sorter, e.g., the features within the DEP separation region of such a cell sorter, however the same fabrication method is readily applied to fabrication of the devices described herein (e.g., on-demand lateral membrane valve). FIGS. 9A through 9ZB are not drawn to scale. In FIGS. 9A through 9P, the Figures depict two different manufacturing streams—the steps in the streams may be largely the same, but the molds used may have different feature sizes. For example, the cross-sections on the left side of each Figure depict the formation of a PDMS layer that may be used to provide a first passage or a second passage, e.g., of a cell sorter, droplet injector, and the like, and the cross-sections on the right side of each Figure may depict the formation of a PDMS layer that may be used to provide a sorting passage of the cell sorter, injection passage of a droplet former, and the like. FIGS. 9Q through 9ZB depict the assembly of the layers into an assembled cell sorter (e.g., as described in copending provisional application No. 61/616,385, filed on Mar. 27, 2012,).

As illustrated in FIG. 9A, a hard substrate may be prepared for etching by depositing or providing a photo-patternable or photo-resistive material on the substrate. Such a material may be, for example, negative photoresist SU8 or positive photoresist AZ4620, and the substrate may, for example, be silicon or glass, although other photoresists or photo-patternable materials may be used as well, as well as other substrate materials. As illustrated in FIG. 9B, an etching operation can remove material from the hard substrate to form a master mold. Alternatively, the raised features on the master mold can be formed by deposition instead of etching. In certain embodiments both etching and deposition can be used to form features on the master mold. As shown in FIG. 9C, the master mold is coated with a conformal silane surface treatment to facilitate later removal of cured PDMS from the molds. In FIG. 9D, uncured PDMS (or other soft lithographic material) may be poured onto the master mold and cured to form a complementary PDMS mold. In FIG. 9E, the PDMS mold may then be separated from the master mold. In FIG. 9F, the PDMS mold may be coated with a conformal silane surface treatment.

As illustrated in FIG. 9G, the PDMS mold may be temporarily set aside and another hard substrate, e.g., silicon or glass, may be prepared by pouring uncured PDMS onto the substrate. In FIG. 9H, the PDMS mold may be retrieved, and in FIG. 9I, the PDMS mold may be pressed into the uncured PDMS on the substrate and the uncured PDMS may then be cured. In FIG. 9J, the PDMS mold may be removed from the cured PDMS on the substrate. The resulting PDMS structure on the substrate may be an exact, or near-exact, duplicate of the master mold and may be referred to herein as a PDMS master mold. It will be recognized that a hard master mold or a "soft" (e.g., PDMS) master mold can be used. A hard master mold will reduce thin film distortion during the molding process. In standard soft lithography, people use SU-8 mold (a hard master mold) to make PDMS structures.

In FIG. 9K, the PDMS master mold may be coated with a CYTOP™ surface treatment to assist in later removal of cast PDMS parts.

Uncured PDMS may be applied to the PDMS master mold (see, e.g., FIG. 9L). The steps discussed above with respect to FIGS. 9A through 9L are similar, in large part, to existing PDMS layer fabrication processes.

FIG. 9M, however, depicts a step that deviates from existing fabrication techniques. In existing fabrication techniques, a PDMS stamping, e.g., a large, flat, featureless base, may be used to compress the uncured PDMS into the PDMS master mold. In one embodiment of the present fabrication technique, however, the PDMS stamping has been modified to include a plate of material within the PDMS that has a much higher modulus than the PDMS (e.g., is stiffer than the PDMS). The plate is located such that a very thin layer of PDMS exists between the plate and the uncured PDMS and the PDMS master mold. This thin layer may be, for example, on the order of 500 microns or less in thickness. In practice, thicknesses of 10 to 30 microns have been found to work well. The plate may be plastic, glass, or other material with a substantially higher modulus than that of PDMS. In practice, plastic plates have proven to be more robust than glass plates. Without being bound to a particular theory, the plate may act as an intermediate load spreader within the PDMS stamping to distribute a compression load across the PDMS master mold and the uncured PDMS. The thin layer of PDMS can allow for very small localized deflections that facilitate full contact between the PDMS mold and the stamping while avoiding the creation of large edge ridges that may appear when a traditional stamping is used.

In one illustrative, but non-limiting embodiment, the embedded-plate stamping shown may be provided by spin-coating the plate with PDMS. However, it was discovered that PDMS exhibits inconsistent curing behavior when applied in too thin a layer. Indeed, in many thin film situations, it was observed that the PDMS does not cure at all and remains in a liquid state. Thus, it was discovered that the PDMS will not reliably set at thicknesses such as those discussed above, resulting in an unreliable manufacturing technique. It was a surprising discovery that if the PDMS that forms the thin layer on the stamping is doped with a catalyst (e.g., a platinum catalyst), however, the PDMS will set reliably regardless of thickness. While catalysts have been used to accelerate cure rate it is believed that such catalysts have not been previously used to reverse a non-cure or inconsistent cure situation, or to prepare PDMS high-temperature processing. Thus, in certain embodiments, the fabrication techniques contemplated herein may include preparing a stamping (this step is not shown) by coating a substantially rigid plate with a thin layer of platinum-doped PDMS. It was discovered that providing platinum ions to the uncured PDMS insures consistent, relatively uniform, curing. It was also surprisingly discovered that with addition of enough platinum ions, the PDMS cured in a short time even at room temperature. In certain embodiments the catalyst is platinum-divinyltetramethyldisiloxane ($C_8H_{18}OPtSi_2$).

The stamping may also have a thicker layer of PDMS on the opposite side of the plate to allow for easy handling or integration with existing equipment, although such a thicker layer is not strictly necessary. The thin layer of PDMS (or the entire PDMS stamping) may be treated with a silane surface treatment, e.g., trichloro(1H,1H,2H,2H-perfluorooctyl)silane (also referred to as "PFOCTS").

In FIG. 9N, the stamping has been compressed against the uncured PDMS and the PDMS master mold and then cured. In FIG. 9O, the cured PDMS layer is removed from the PDMS master mold by pulling the stamping away from the PDMS master mold. Due to the higher bond strength in silane-treated surfaces as compared with CYTOP-treated surfaces, the PDMS layer will stay bonded to the stamping, allowing for easy transfer to other structures.

FIG. 9P depicts the removed PDMS layer bonded to the stamping; the PDMS layer may be treated with an oxygen plasma to facilitate later bonding with a glass or PDMS structure. In FIG. 9Q, one of the PDMS layers is positioned over a prepared glass substrate; the glass substrate may, for example, be prepared by coating it with an electrically-conductive coating such as ITO so that it may act as an electrode layer of a DEP cell sorter. In FIG. 9R, the PDMS layer may be directly bonded to the glass substrate as a result of the oxygen plasma treatment of the PDMS layer. In FIG. 9S, the stamping may be removed—due to the higher bond strength of the direct bonding via oxygen plasma treatment as compared with the bond across the silane-treated surfaces, the PDMS layer may separate from the stamping and remain cleanly attached to the glass substrate. The PDMS layer placed on the substrate in this case corresponds to a sublayer of an electrically-insulating layer in a DEP cell sorter having a first or second passage in it.

In FIG. 9T, another PDMS layer (in one embodiment time corresponding with a sublayer of an electrically-insulating layer in a DEP cell sorter having a sorting passage in it), may be positioned over the previously-placed PDMS layer using the stamping to which it is attached. This second PDMS layer may also be treated with an oxygen plasma to facilitate direct bonding to the previously-placed PDMS layer. In FIG. 9U, the second PDMS layer may be directly bonded to the first PDMS layer by compressing it into the first PDMS layer with the stamping. In FIG. 9V, the stamping may be removed in much the same manner as in FIG. 9S.

In FIG. 9W, a third PDMS layer, in this case similar to the first PDMS layer, may be positioned over the first and second PDMS layers. The third PDMS layer, as with the other PDMS layers, may be treated with an oxygen plasma. In FIG. 9X, the third PDMS layer may be directly bonded to the second PDMS layer to form a three-layer stack of PDMS layers that are fused into one, essentially contiguous, structure. In FIG. 9Y, the stamping may be removed, leaving the 3-layer PDMS structure behind. In FIG. 9Z, the exposed top of the PDMS structure may be prepared for bonding to another hard substrate, e.g., glass. In FIG. 9ZA, the hard substrate may be positioned over the assembled PDMS stack, and in FIG. 9ZB, the hard substrate may be bonded to the stack.

In various embodiments the resulting structure provides very clean inter-layer via features, and is particularly well-suited for microfluidic devices. The above technique may be modified as needed to omit certain steps, add other steps, and otherwise tailor the technique for particular design requirements. For example, it may be possible to form features with stepped cross-sections in the molds, thus reducing the number of individual layers that must be made and bonded together. While the depicted technique was shown for a 3-layer stack of PDMS layers, more or less PDMS layers may be manufacturing in this manner and assembled into a PDMS layer stack.

II. Pulse Laser Induced on-Demand Membrane Valve Droplet Generation

Figure 2:
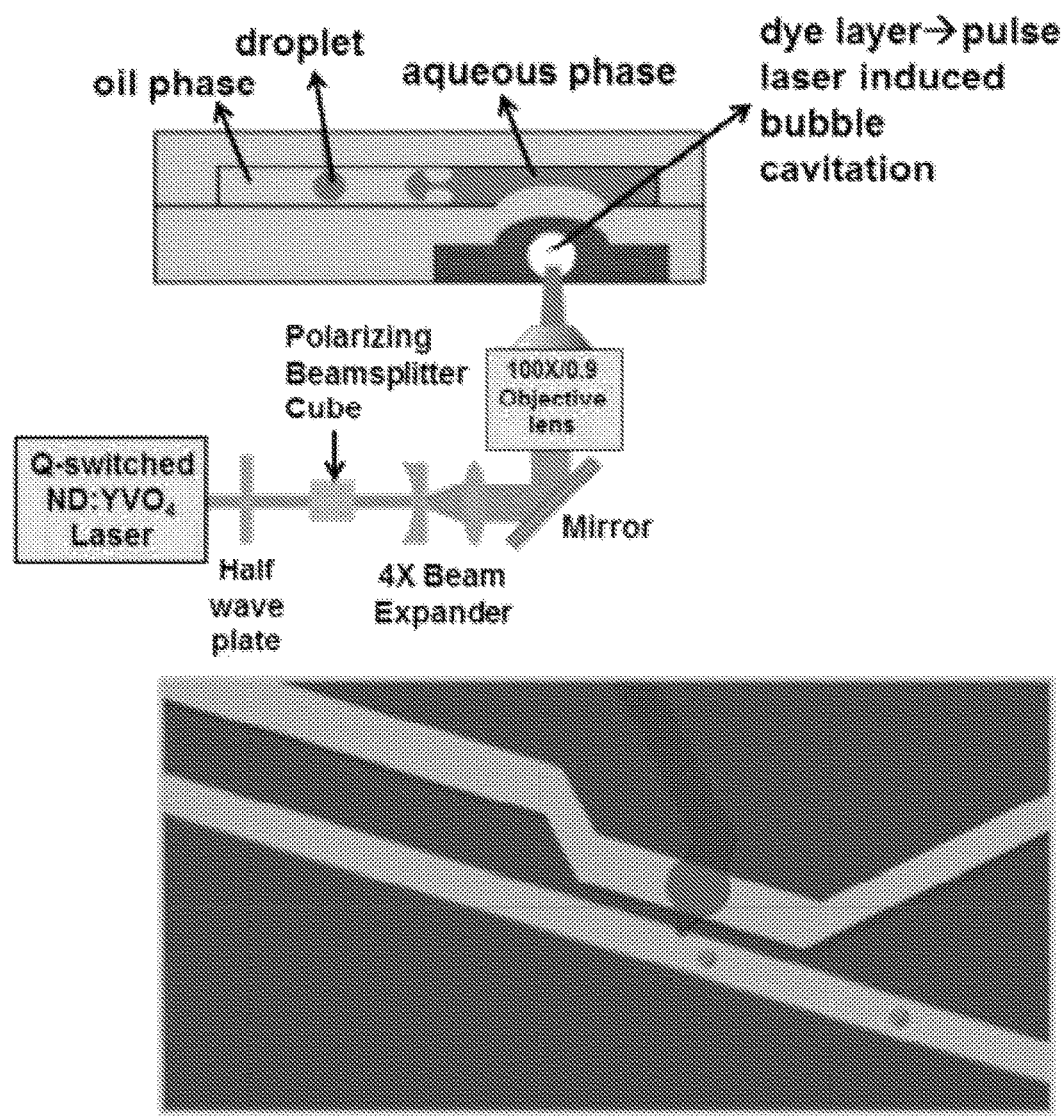
FIG. 2 schematically illustrates pulse laser induced on-demand membrane valve droplet generation. A PDMS thin membrane is used to totally separate the pulse laser induced contamination. The induced bubble can deform the membrane into the aqueous channel, break the stable water-oil interface, and squeeze out a picoliter droplet into the oil channel.

FIG. 2 schematically illustrates an embodiment of a pulse laser driven membrane valve droplet generator. A thin membrane (e.g., a PDMS membrane) is used to separate a dye channel for laser excitation from the sample channel to prevent potential contamination from pulse laser induced reactive chemicals.

Figure 4:
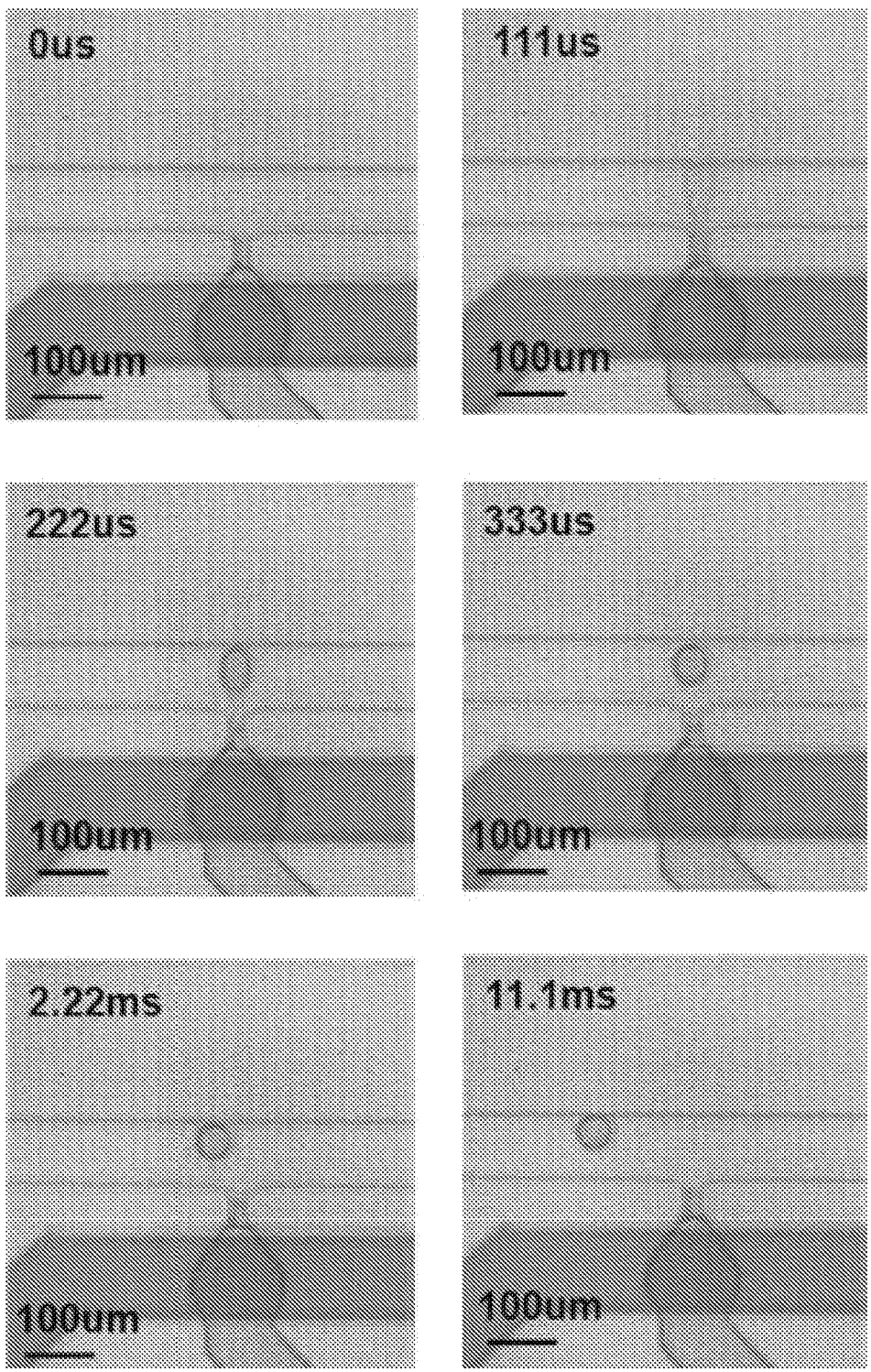
FIG. 4 shows snapshots of the droplet generation process.

Each laser pulse can trigger a cavitation bubble to deform the membrane to squeeze out a droplet through the nozzle into the oil phase. Instead of using continuous phase flow that consumes huge amount of reagents, a static pressure source can be used to maintain the stable (e.g., water-oil) interface. This approach dramatically reduces the consumption of expensive and precious reagents. After a single droplet is ejected into the oil phase, the interface can automatically recover to its original location in a very short time period since the membrane is only partially and locally deformed. The droplet generation rate can go up to hundreds of Hz. The volume of droplets produced on certain embodiments of this platform is around 80 pL as shown in FIG. 4.

Various embodiments of the devices described herein incorporate microchannels (microfluidic channels). The terms "microfluidic channel" or "microchannel" are used interchangeably and refer to a channel having at least one characteristic dimension (e.g., width or diameter) less than 1,000 µm, more preferably less than about 900 µm, or less than about 800 µm, or less than about 700 µm, or less than about 600 µm, or less than about 500 µm, or less than about 400 µm, or less than about 300 µm, or less than about 250 µm, or less than about 200 µm, or less than about 150 µm, or less than about 100 µm, or less than about 75 µm, or less than about 50 µm, or less than about 40 µm, or less than about 30 µm, or less than about 20 µm.

In certain embodiments the methods and devices described herein may utilize immiscible fluids. In this context, the term "immiscible" when used with respect to two fluids indicates that the fluids when mixed in some proportion, do not form a solution. Classic immiscible materials are water and oil. Immiscible fluids, as used herein also include fluids that substantially do not form a solution when combined in some proportion. Commonly the materials are substantially immiscible when they do not form a solution if combined in equal proportions. In certain embodiments immiscible fluids include fluids that are not significantly soluble in one another, fluids that do not mix for a period of time due to physical properties such as density or viscosity, and fluids that do not mix for periods of time due to laminar flow.

In addition, such fluids are not restricted to liquids but may include liquids and gases. Thus, for example, where the droplets are to be formed comprising an aqueous solvent (such as water) any number of organic compounds such as carbon tetrachloride, chloroform, cyclohexane, 1,2-dichloroethane, dichloromethane, diethyl ether, dimethyl formamide, ethyl acetate, heptane, hexane, methyl-tert-butyl ether pentane, toluene, 2,2,4-trimethylpentane, and the like are contemplated. Various mutually insoluble solvent systems are well known to those skilled in the art (see e.g. Table 1). In another example, droplets of aqueous buffer containing physiologically normal amounts of solute may be produced in a dense aqueous buffer containing high concentrations of sucrose. In yet another example, droplets of an aqueous buffer containing physiologically normal amounts of solute may be produced in a second aqueous buffer containing physiologically normal amounts of solute where the two buffers are segregated by laminar flow. In still another example, droplets of a fluid may be produced in a gas such as nitrogen or air.

diameter, and outer diameter of such a nozzle can be optimized to control droplet size, droplet uniformity, mixing at the fluid interface, or a combination of these.

In certain embodiments the droplet generation and/or droplet merger components described herein may be provided on a substrate that differs from the material that comprises the fluid channels. For example, the fluid chan-

TABLE 1 illustrates various solvents that are either miscible or immiscible in each other. The solvent on left column does not mix with solvents on right column unless otherwise stated.

| Solvents | Immiscibility |
|---|---|
| Acetone | can be mixed with any of the solvents listed in the column at left |
| Acetonitrile | cyclohexane, heptane, hexane, pentane, 2,2,4-trimethylpentane |
| carbon tetrachloride | can be mixed with any of the solvents listed in the column at left except water |
| chloroform | can be mixed with any of the solvents listed in the column at left except water |
| cyclohexane | acetonitrile, dimethyl formamide, dimethyl sulfoxide, methanol, water |
| 1,2-dichloroethane | can be mixed with any of the solvents listed in the column at left except water |
| dichloromethane | can be mixed with any of the solvents listed in the column at left except water |
| diethyl ether | dimethyl sulfoxide, water |
| dimethyl formamide | cyclohexane, heptane, hexane, pentane, 2,2,4-trimethylpentane, water |
| dimethyl solfoxide | cyclohexane, heptane, hexane, pentane, 2,2,4-trimethylpentane, diethyl ether |
| 1,4-dioxane | can be mixed with any of the solvents listed in the column at left |
| ethanol | can be mixed with any of the solvents listed in the column at left |
| ethyl acetate | can be mixed with any of the solvents listed in the column at left except water |
| heptane | acetonitrile, dimethyl formamide, dimethyl sulfoxide, methanol, water |
| hexane | acetonitrile, dimethyl formamide, dimethyl sulfoxide, methanol, acetic acid, water |
| methanol | cyclohexane, heptane, hexane, pentane, 2,2,4-trimethylpentane |
| methyl-tert-butyl ether | can be mixed with any of the solvents listed in the column at left except water |
| pentane | acetonitrile, dimethyl formamide, dimethyl sulfoxide, methanol, water, acetic acid |
| 1-propanol | can be mixed with any of the solvents listed in the column at left |
| 2-propanol | can be mixed with any of the solvents listed in the column at left |
| tetrahydrofuran | can be mixed with any of the solvents listed in the column at left |
| toluene | can be mixed with any of the solvents listed in the column at left except water |
| 2,2,4-trimethylpentane | acetonitrile, dimethyl formamide, dimethyl sulfoxide, methanol, water |
| water | carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, 2,2,4-trimethylpentane |

In certain embodiments the first fluid and second fluid need not be immiscible in each other. In such embodiments, injected droplets can be kept separate from each other simply by adjusting flow rates in the microchannels and rate of bubble formation to form separated bubbles.

In various embodiments the droplets generated by the devices and methods described herein can contain or encapsulate a wide variety of materials. In some embodiments the droplets may contain test samples, cells, organelles, proteins, nucleic acids, enzymes, PCR or other testing reagents, biochemicals, dyes, or particulates (for example polymeric microspheres, metallic microparticles, or pigments). In still other embodiments a droplet may encapsulate one or more previously generated droplets. In addition, the invention need not be limited to aqueous droplet systems. For example, such droplet generating methods and devices may be used in nanoparticle coating, where materials in organic solvents can be used to deposit layers on or encapsulate nanoparticles.

As noted above, in some embodiments an opening in a fluid channel can be configured as a nozzle. The depth, inner nels may be fabricated using an elastomeric material that is disposed upon a rigid surface. Suitable fluid channel materials include but are not limited to flexible polymers such as PDMS, plastics, and similar materials. Fluid channels may also be comprised of nonflexible materials such as rigid plastics, glass, silicon, quartz, metals, and similar material. Suitable substrates include but are not limited to transparent substrates such as polymers, plastic, glass, quartz, or other dielectric materials. Other suitable substrate materials include but are not limited to nontransparent materials such as opaque or translucent plastics, silicon, metal, ceramic, and similar materials.

The parameters described above and in the Examples (e.g., flow rate(s), laser intensity, laser frequency/wavelength, channel dimensions, port/nozzle dimensions, channel wall stiffness, location of cavitation bubble formation, and the like) can be varied to optimize droplet formation and/or droplet/particle/cell encapsulation for a particular desired application.

There are a number of formats, materials, and size scales that may be used in the construction of the droplet generating devices described herein and in microfluidic devices that may incorporate them. In some embodiments the droplet generating devices and the connecting fluid channels are comprised of PDMS (or other polymers), and fabricated using soft lithography. PDMS is an attractive material for a variety of reasons, including but not limited to low cost, optical transparency, ease of molding, and elastomeric character. PDMS also has desirable chemical characteristics, including compatibility with both conventional siloxane chemistries and the requirements of cell culture (e.g. low toxicity, gas permeability). In an illustrative soft lithography method, a master mold is prepared to form the fluid channel system. This master mold may be produced by a micromachining process, a photolithographic process, or by any number of methods known to those with skill in the art. Such methods include, but are not limited to, wet etching, electron-beam vacuum deposition, photolithography, plasma enhanced chemical vapor deposition, molecular beam epitaxy, reactive ion etching, and/or chemically assisted ion beam milling (Choudhury (1997) *The Handbook of Microlithography, Micromachining, and Microfabrication*, Soc. Photo-Optical Instru. Engineer.; Bard & Faulkner, *Fundamentals of Microfabrication*).

Once prepared the master mold is exposed to a pro-polymer, which is then cured to form a patterned replica in PDMS. The replica is removed from the master mold, trimmed, and fluid inlets are added where required. The polymer replica may be optionally be treated with a plasma (e.g. an $O_2$ plasma) and bonded to a suitable substrate, such as glass. Treatment of PDMS with $O_2$ plasma generates a surface that seals tightly and irreversibly when brought into conformal contact with a suitable substrate, and has the advantage of generating fluid channel walls that are negatively charged when used in conjunction with aqueous solutions. These fixed charges support electrokinetic pumping that may be used to move fluid through the device. While the above described fabrication of a droplet generating device using PDMS, it should be recognized that numerous other materials can be substituted for or used in conjunction with this polymer. Examples include, but are not limited to, polyolefin plastomers, perfluoropolyethylene, polyurethane, polyimides, and cross-linked phenol/formaldehyde polymer resins.

In some embodiments single layer devices are contemplated. In other embodiments multilayer devices are contemplated. For example, a multilayer network of fluid channels may be designed using a commercial CAD program. This design may be converted into a series of transparencies that is subsequently used as a photolithographic mask to create a master mold. PDMS cast against this master mold yields a polymeric replica containing a multilayer network of fluid channels. This PDMS cast can be treated with a plasma and adhered to a substrate as described above.

As noted above, the methods and devices described herein are particularly suitable for use in microfluidic devices. In some embodiments therefore the fluid channels are microchannels. Such microchannels have characteristic dimensions ranging from about 100 nanometers to 1 micron up to about 500 microns. In various embodiments the characteristic dimension ranges from about 1, 5, 10, 15, 20, 25, 35, 50 or 100 microns up to about 150, 200, 250, 300, or 400 microns. In some embodiments the characteristic dimension ranges from about 20, 40, or about 50 microns up to about 100, 125, 150, 175, or 200 microns. In various embodiments the wall thickness between adjacent fluid channels ranges from about 0.1 micron to about 50 microns, or about 1 micron to about 50 microns, more typically from about 5 microns to about 40 microns. In certain embodiments the wall thickness between adjacent fluid channels ranges from about 5 microns to about 10, 15, 20, or 25 microns.

In various embodiments the depth of a fluid channel ranges from 5, 10, 15, 20 microns to about 1 mm, 800 microns, 600 microns, 500 microns, 400 microns, 300 microns, 200 microns, 150 microns, 100 microns, 80 microns, 70 microns, 60 microns, 50 microns, 40 microns, or about 30 microns. In certain embodiments the depth of a fluid channel ranges from about 10 microns to about 60 microns, more preferably from about 20 microns to about 40 or 50 microns. In some embodiments the fluid channels can be open; in other embodiments the fluid channels may be covered.

As noted above, some embodiments a nozzle is present. In certain embodiments where a nozzle is present, the nozzle diameter can range from about 0.1 micron, or about 1 micron up to about 300 microns, 200 microns, or about 100 microns. In certain embodiments the nozzle diameter can range from about 5, 10, 15, or 20 microns up to about 25, 30, 35, 40, 45, 50, 55, 60, 65, 70, 75, or about 80 microns. In some embodiments the nozzle diameter ranges from about 1, 5, 10, 15, or 20 microns to about 25, 35, or 40 microns.

In some embodiments the methods and devices described herein can generate droplets at a rate ranging from zero droplets/sec, about 2 droplets/sec, about 5 droplets/sec, about 10 droplets/sec, about 20 droplets/sec, about 50 droplets/sec, about 100 droplets/sec, about 500 droplets/sec, or about 1000 droplets/sec, up to about 1,500 droplets/sec, about 2,000 droplets/sec, about 4,000 droplets/sec, about 6,000 droplets/sec, about 8,000 droplets/sec, about 10,000 droplets/sec, about 20,000 droplets/sec, about 50,000 droplets/sec, and about 100,000 droplets/sec.

In various embodiments the devices and methods described herein can generate droplets having a substantially continuous volume. Droplet volume can be controlled to provide volumes ranging from about 0.1 fL, about 1 fL, about 10 fL, and about 100 fL to about 1 microliter, about 500 nL, about 100 nL, about 1 nL, about 500 pL or about 200 pL. In certain embodiments volume control of the droplet ranges from about 1 pL to about 150 pL, about 200 pL, about 250 pL, or about 300 pL.

As indicate above, the microchannel droplet formation/merger injection devices described herein can provide a system integrated with other processing modules on a microfluidic "chip" or in flow through fabrication systems for microparticle coating, microparticle drug carrier formulation, and the like. These uses, however, are merely illustrative and not limiting.

Microfluidic devices can manipulate volumes as small as several nanoliters. Because the microfluidic reaction volume is close to the size of single mammalian cells, material loss is minimized in single-cell mRNA analysis with these devices. The ability to process live cells inside microfluidic devices provides a great advantage for the study of single-cell transcriptomes because mRNA is rapidly degraded with cell death. A highly integrated microfluidic device, having 26 parallel 10 nL reactors for the study of gene expression in single human embryonic stem cells (hESC) has been reported (Zhong et al. (2008) *Lab on a Chip*, 8: 68-74; Zhong et al. (2008) *Curr. Med. Chem.*, 15: 2897-2900). In various microfluidic devices all systems for obtaining single-cell cDNA including cell capture, mRNA capture/purification, cDNA synthesis/purification, are performed inside the device. The present devices and methods offer effective means of encapsulating and and/or separating individual cells for, e.g., further processing, Any of a number of approaches can be used to convey the fluids, or mixtures of droplets, particles, cells, etc. along the channels of the devices described herein. Such approaches include, but are not limited to gravity flow, syringe pumps, peristaltic pumps, electrokinetic pumps, bubble-driven pumps, and air pressure driven pumps.

Figure 6:
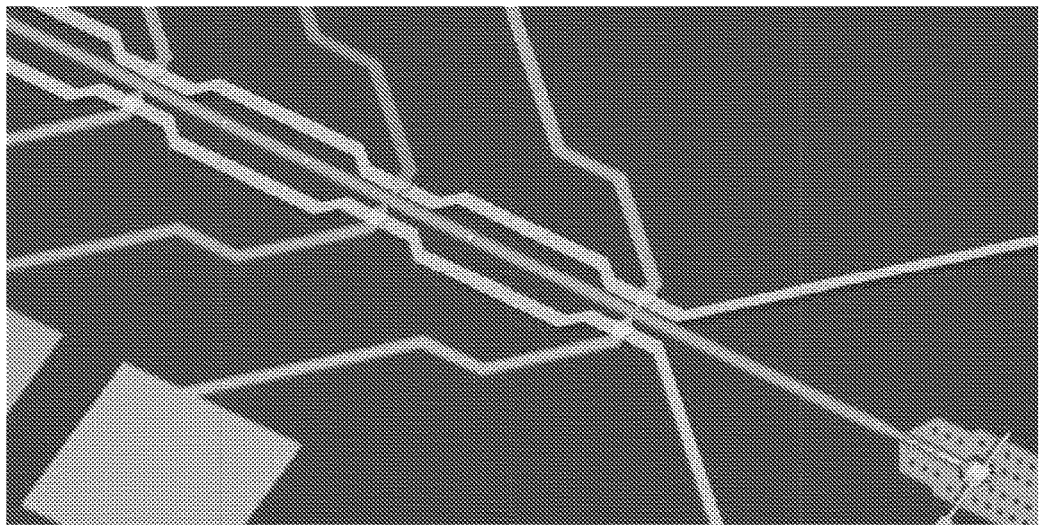
FIG. 6 schematically illustrates one embodiment of a platform with parallel droplet generators and the downstream droplet merger for generating droplets with multiplexed drug/chemical combinations FIG. 7 schematically illustrates one embodiment of a platform integrating uFACS and multiple droplet generators for high-speed single cell encapsulation and single cell analysis.

In certain illustrative but non-limiting embodiments two major applications of the platforms described herein are contemplated. These include:

1. Rapid production of a large combinatorial cocktail drug library: A 2D scanning mirror coupled with a high repetition rate pulse laser can support parallel droplet generators deployed on the same microfluidic chip (see, e.g., FIG. 6). The 3D microfluidic fabrication technique described herein can solve the cross interconnet issues found in 2D microfluidics and enable 3D microchannel routing to support up to hundreds of sample channels on the same chip for producing a large multiplexed combinatorial library. Producing a large library with 1 million different chemical combinations may take less than 3 hours (100 combinations/sec).

Figure 7:
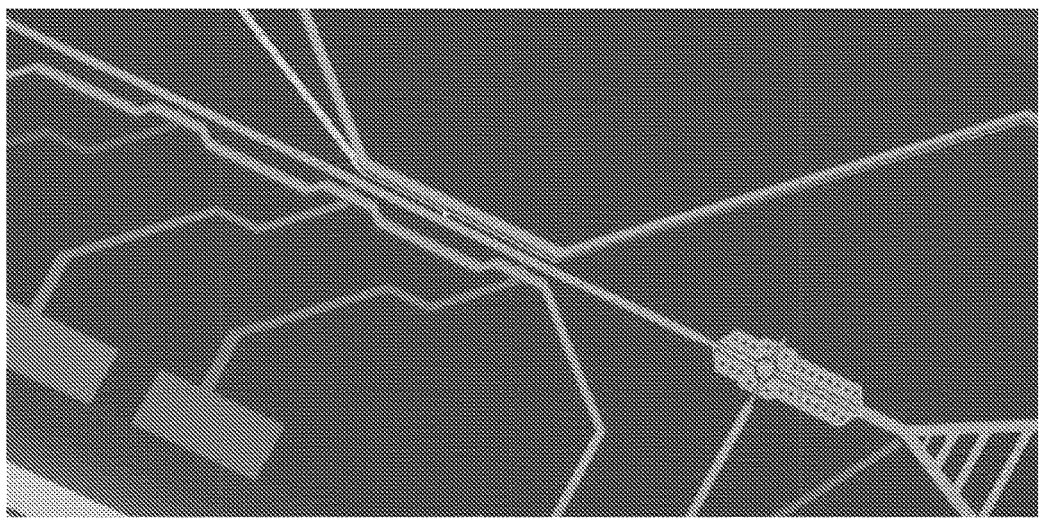

2. The droplet generation and merging platform described herein can be readily integrated with our PLACS system described in U. S. Patent Publication No: 2012/0236299 to enable high speed single cell encapsulation and downstream merging of the cell captured droplets with other biochemical reagents such as cell lysing buffers, primers, and other PCR buffers for single cell PCR analysis (FIG. 7). This integrated system will enable the first high throughput FACS system that can simultaneously provide not only optical signatures of single cells but also the molecular level analysis data such as mRNA expression levels.

While various implementations have been described herein, it should be understood that they have been presented by way of example only, and not limitation. Thus, the breadth and scope of the present disclosure should not be limited by any of the implementations described herein, but should be defined only in accordance with the following and later-submitted claims and their equivalents. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. However, where a definition or use of a term in a reference, which is incorporated by reference herein, is inconsistent or contrary to the definition of that term provided herein, the definition of that term provided herein applies and the definition of that term in the reference does not apply. The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A microfluidic droplet merger component, said component comprising:
    a central channel comprising a plurality of elements disposed on both sides of said central channel and spaced to create a plurality of lateral passages on both sides of said central channel that drain a carrier fluid out of a fluid stream comprising droplets of a first fluid contained in said carrier fluid; and
    a deformable lateral membrane valve disposed to and configured to control the width of said central channel, wherein said lateral membrane valve is disposed downstream from said plurality of elements.

2. The droplet merger component of claim 1, wherein the width of said central channel reduces as a function of distance downstream through said plurality of lateral passages.

3. The droplet merger component of claim 1, wherein the width of said lateral passages is smaller than the width of said central channel at the same location and smaller than the average diameter of a droplet in the central channel.

4. The droplet merger component of claim 1, wherein said plurality of elements comprise a micropillar array.

5. The droplet merger component of claim 4, wherein said micropillar array comprises pairs of pillars that form lateral channels slanted in a downstream direction.

6. A device for the manipulation of microfluidic droplets, said device comprising a substrate carrying or comprising:
    one or more droplet merger components according to claim 1; and
    optionally one or more droplet generators.

7. The device of claim 6, wherein said device further comprises a controller that controls the amount and timing of constriction of said membrane valve.

8. The device of claim 6, wherein said device comprises at least two droplet generators, or at least 4 droplet generators.

9. The device of claim 8, wherein a plurality of droplet generators are configured to share a common second microfluidic channel and to inject droplets into said common second microfluidic channel.

10. The device of claim 9, wherein a droplet merger component is disposed to receive and merge droplets from said common second microfluidic channel.

11. A method of combining droplets in a microfluidic system, said method comprising providing a plurality of droplets flowing through a microfluidic channel into the central channel(s) of one or more droplet merger components according to claim 1 causing the merger of a plurality of droplets.

12. The method of claim 11, wherein said method comprises varying the constriction created by said lateral membrane valve to control the timing of droplet merger and/or the number of merged droplets.

* * * * *